(12) United States Patent
Nikolaev et al.

(10) Patent No.: US 8,017,341 B2
(45) Date of Patent: Sep. 13, 2011

(54) TRANSCRIPTION FACTORS

(75) Inventors: Igor Nikolaev, Copenhagen (DK); Susan Mampusti Madrid, Vedbaek (DK)

(73) Assignee: Danisco A/S, Copenhagen (DK)

( * ) Notice: Subject to any disclaimer, the term of this patent is extended or adjusted under 35 U.S.C. 154(b) by 844 days.

(21) Appl. No.: 11/738,355

(22) Filed: Apr. 20, 2007

(65) Prior Publication Data

US 2007/0254336 A1 Nov. 1, 2007

Related U.S. Application Data

(63) Continuation-in-part of application No. PCT/IB2005/003600, filed on Nov. 10, 2005.

(51) Int. Cl.
*C12Q 1/68* (2006.01)
*C12N 15/00* (2006.01)
*C12N 1/15* (2006.01)
*C07H 21/04* (2006.01)

(52) U.S. Cl. .................. 435/6.15; 435/69.1; 435/254.11; 536/24.1

(58) Field of Classification Search .................. None
See application file for complete search history.

(56) References Cited

FOREIGN PATENT DOCUMENTS

| EP | 0 599 646 | 6/1994 |
|----|-----------|--------|
| EP | 0 606 621 | 7/1994 |
| EP | 0 832 974 | 4/1998 |
| EP | 1 514 936 | 3/2005 |
| WO | WO 97/00962 | 1/1997 |
| WO | WO 99/25735 | 5/1999 |
| WO | WO 01/20007 | 3/2001 |

OTHER PUBLICATIONS

Database *Aspergillus*: Accession No. AN0388.2: Mar. 2003, Hypothetical Protein.
Database EMBL: Accession No. EM_PRO: CO134487: EST829158 *Aspergillus flavus* Normalized cDNA Expression Library *Aspergillus flavus* cDNA Clone NAFAT01 5' End Similar to Transcriptional Activator x1nR (*Aspergillus niger*) mRNA Sequence, Jun. 18, 2004.
Noel N. M.E. van Peij, et al., The Transcriptional Activator X1nR Regulates Both Xylanolytic and Endoglucanase Gene Expression in *Aspergillus niger*, Applied and Environmental Microbiology (1998) vol. 64, No. 10, p. 3615-3619.
Ronald P. De Vries, et al., *Aspergillus* Enzymes Involved in Degradation of Plant Cell Wall Polysaccharides, Microbiology and Molecular Biology Reviews, (2001) vol. 65, No. 4, p. 497-522.
E. A. Vavilova et al., "Mechanism of Overproduction of Secreted Enzymes in the Mycelial Fungus *Penicillium canescens*" Applied Biochemistry and Microbiology, vol. 39, No. 3, pp. 249-256, 2003.
Ronald P. deVries et al., "Characterization of an *Aspergillus nidulans* L-arabitol dehydrogenase mutant", FEMS Microbiology Letters, vol. 123, No. (1-2), pp. 83-90, 1994.
Marco J. L. de Groot et al., "Isolation and characterization of two specific regulatory *Aspergillus niger* mutants shows antagonistic regulation of arabinan and xylan metabolism" Microbiology, vol. 149, No. 5, pp. 1183-1191, 2003.
Peter Richard et al., "Cloning and Expression of a Fungal L-Arabinitol 4-Dehydrogenase Gene", The Journal of Biological Chemistry, vol. 276, No. 44, pp. 40631-40637, 2001.
Bernhard Seiboth et al., "D-Xylose Metabolism in *Hypocrea jecorina*: Loss of the Xylitol Dehydrogenase Step Can Be Partially Compensated for by *lad I-* Encoded L-Arabinitol-4-Dehydrogenase", Eukaryotic Cell. vol. 2, No. 5, pp. 867-875, 2003.
Erzsebet Fekete et al., "The alternative D-galactose degrading pathway of *Aspergillus nidulans* proceeds via L-sorbose", Arch Microbiol, vol. 181, No. 1, pp. 35-44, 2004.
Pail et al., "L-arabinitol dehydrogenases of Hypocrea jecorina and *Aspergillus nidulans* proceeds via L-sorbose" Abstract of the European Conference of Fungal Genetics, vol. 7, Copenhagen, 2004.
Database EMBL [Online] Jun. 18, 2004, "EST829158 *Aspergillus flavus* Normalized cDNA Expression Library *Aspergillus flavus* cDNA clone NAFATO1 5" end similar to Transcriptional activator x1nR. {*Aspergillus niger*}, mRNA sequence X 002383671 retroeved frp, EBA accessopm mp/ E,-PRO:C0134487/ Database accession No. C0134487.
Database *Aspergillus* [Online] Broad Institute of MIT and Harvard; *Aspergillus* Sequencing Project Mar. 2003, "(AN0388.2) hypothetical protein" XP002383672 retrieved from www.Broad/mit/edu/cgi-bin/annotation_/aspergillus/findfeatures.cgi accession No. AN0388.2.
R.P. De Vries et al.: "*Aspergillus* enzymes involved in degradation of plant cell wall polysaccharides", Microbiology and Molecular Biology Reviews, American Society for Microbiology, vol. 65, No. 4, Dec. 2001, pp. 497-522.
T. Shibata et al: Purification and Molecular Characterization of a Quinoprotein Alcohol Dehydrogenase from *Pseudogluconobacter saccharoketogenes* IFO 14464, Journal of Biosciences and Bioengineering, vol. 92, No. 6, pp. 524-531 (2001).
T. Ishiguro et al: Synthesis of branched cyclomaltooligosaccharide carboxylic acids (cyclodextrin carboxylic acids) by microbial oxidation, Carbohydrate Research, vol. 331, pp. 423-430 (2001).
R. P. De Vries: Regulation of *Aspergillus* genes encoding plant cell wall polysaccharide-degrading enzymes; relevance for industrial production, Applied Microbiology Biotechnology, 2003, vol. 61, No. 1, pp. 10-20.

(Continued)

*Primary Examiner* — Michele Joike
(74) *Attorney, Agent, or Firm* — Vedder Price P.C.; Thomas J. Kowalski; Smitha B. Uthaman

(57) ABSTRACT

The present invention relates to an isolated nucleic acid sequence coding for a PntR transcription factor comprising a nucleotide sequence that is the same as, or is complementary to, or contains any suitable codon substitutions for any of those of SEQ ID NOs: 1, 3 or 5 or comprises a sequence which has at least 60% sequence homology with any of SEQ ID NOs: 1, 3 or 5, as well as corresponding polypeptides, vector systems and host cells comprising the same. In particular, the invention relates to sequences which are obtained from an *Aspergillus*, *Trichoderma* or *Penicillium* cell. The invention further relates to methods for disrupting PntR expression in a cell as well as methods for expression or production of a POI in a host cell in which PntR expression has been disrupted.

13 Claims, 19 Drawing Sheets

OTHER PUBLICATIONS

N. Aro et al: Transcriptional regulation of plant cell wall degradation by filamentous fungi, FEMS Microbiology Reviews, vol. 29, No. 4, pp. 719-739, (2005).

N. N. Van Peij et al:, Isolation and analysis of *xln*R, encoding a transcriptional activator co-coordinating xylanoltyic expression in *Aspergillus niger*, Molecular Microbiology, 1998, vol. 27, No. 1, pp. 131-142.

**SEQ ID NO: 1 (The coding sequence of the *pntR* gene from *A. nidulans*).**

```
   1 atggcatcct cccaccaggg gaacgggaca gtccccaact ctcagaccga cgcacccccg
  61 gattcctcca caaagcgccg atggaggcgc aaccgtatag cttgtgactc ttgtcatgct
 121 cgccgcgttc gatgcgaccg ccagtttccg tgctcgcgct gcctccgtag cgagatcacc
 181 tgcgaattca cgcgcgagcg tcgtaagcga ggccgtatcg cacgatccaa gctggccgaa
 241 atggcaaaga acaaaatgga gaccagtgag acgccggctc cggctaagac catgaatggt
 301 ataccggcgc ccgctggtac agagatccca gggcatgtct ccccgcatc gactttccac
 361 catcgatcgc cgccggcaaa tgctcctact gtttctgctc caagtgttga tggccgacgg
 421 tctcagactg acccacaact tcccgtccgg agaccagaaa tcggcgggaa tgttactgag
 481 gaatggctcg ccgggacgca tgtatcacca ggatcatacg agttcttgaa tggaccagct
 541 tttggagaag gactaggacc gtttcctcac atgttcgatg tatggaacgg tgtcgacctg
 601 gccgcctaca gcgctgggac ttcgcaaggg tcgaaagcga ccaacgcgcc gtcaacctct
 661 acagcaccgt tgaagtaccc ggttctacag cccttgatgc cgttcgtgga ggcgactctg
 721 cctcgaaaac tggtctttga cctgcttgat ctatatttca ccagcgcgtt ttcaactcac
 781 atgcacccg tatgccatca tattcattgc tatgtgctgc ggaaggtttc cttcctcagc
 841 aaagatgcgc cacgacccag cagtccggca ctgctttcga gtatgctctg ggtagctgct
 901 ctggatgata gggcgttttc gttgccgatt tcgcctccgc agcggaaaag gatctgccaa
 961 tttctctgcg ctctcactat ccgcttgttg cgaccgttga ttcatgtttc cttcaaagat
1021 cagggcggcg ccgcagcagc ggttgcagca gcggccgcgg cggccaccaa tacccagcg
1081 ttcgccggcg tcggccagga tctaccgccc actactgtgc accatccgtt tgaaggagga
1141 ggagacgata gaggcctggt agggccggca ggctcgcttg acgatgtgat tacctacatc
1201 catgtagctt ctatcatctc gtccagtgag cagaaggcag ccagtatgcg atggtggcat
1261 gcggccttca ccctagcgcg agagctcaag ctaaatcaag agatcgaggt gatgccgaat
1321 ggcgactccc aagtggaagg gtcaagtccg ccgttcggat actctctacc cggctgggat
1381 ggggctgacc cgggccccgt ctttaattac tcaaacccaa ctcggtccag tctcaattgc
1441 gtctgtgatc gccaggacca gaacaccatc accgaagagc accgcgaaga acggcggcgg
1501 acatggtggc ttctgtacat catggaccgc catctcgcac tgtgctacaa ccggccgttg
1561 gccttgctgg atgccgaaag cgaagactta ctactaccgc tggacgaggc atcctggcag
1621 tcagggatca tacacagtaa cagcccgaag tcggatgggc cgcaatgcct actctctgcc
1681 gacaagaaca agcgtcgcct gtttccgaac ttcatctgcc atgatcattc tgtgtttggc
1741 tttttccttc ccctcatgac gatcaccggc gaactcattg acctgaacca agcgaggaac
1801 catccgatgc ttggcatgcg actaaacggc aaggacgcgt ggaatgtcca tgtaagcgaa
1861 gttctacgcc agctcgagat ctacaaggct agcttaacca cgttcgccgc tactacatcc
1921 gatccggaag cgccgctgtc cgcttatgcg cacgcccaat ccgaacatct accagccgag
```

FIGURE 16B

```
1981 ccatccctct cgcaagcata cgcatggcac acgcaaactg tcatatcgta tgcatcatac
2041 ctggtccacg tgctccacat cctgttggtg ggcaaatggg atcccgtatc cctgatcgag
2101 gacaaagatt tctggacctc ctcccccgca ttcgcatcga ccatctcgca tgcgctggac
2161 gcagccgact cggtcgatca gattctccga tacgacccag acattagttt catgccctat
2221 ttctttggca ttcagttgct gcaaggcagt tttcttctcc tgctgatcgt tgagaggctg
2281 cagaaggaag cgggcgaagg aatccttaat gcatgcgagg tgatgatccg agctacggaa
2341 tcttgtgtgg tgactctgaa caccgaatac cagcgaaatt ccggcaggt catgcgcagt
2401 gccgttgccc aagcacgagg gaggccagtc aatcacagcg agattcgcca ccggcgcaag
2461 gctgtgctag cgctgtaccg gtggacaagg aagggaaccg ggttggctct ctag
```

FIGURE 17

SEQ ID NO:2 (The deduced primary structure from the *pntR* gene from *A. nidulans*)

```
  1    MASSHQGNGT  VPNSQTDAPP  DSSTKRRWRR  NRIACDSCHA  RRVRCDRQFP
 51    CSRCLRSEIT  CEFTRERRKR  GRIARSKLAE  MAKNKMETSE  TPAPAKTMNG
101    IPAPAGTEIP  GHVSPASTFH  HRSPPANAPT  VSAPSVDGRR  SQTDPQLPVR
151    RPEIGGNVTE  EWLAGTHVSP  GSYEFLNGPA  FGEGLGPFPH  MFDVWNGVDL
201    AAYSAGTSQG  SKATNAPSTS  TAPLKYPVLQ  PLMPFVEATL  PRKLVFDLLD
251    LYFTSAFSTH  MHPVCHHIHC  YVLRKVSFLS  KDAPRPSSPA  LLSSMLWVAA
301    LDDRAFSLPI  SPPQRKRICQ  FLCALTIRLL  RPLIHVSFKD  QGGAAAAVAA
351    AAAAATNNPA  FAGVGQDLPP  TTVHHPFEGG  GDDRGLVGPA  GSLDDVITYI
401    HVASIISSSE  QKAASMRWWH  AAFTLARELK  LNQEIEVMPN  GDSQVEGSSP
451    PFGYSLPGWD  GADPGPVFNY  SNPTRSSLNC  VCDRQDQNTI  TEEHREERRR
501    TWWLLYIMDR  HLALCYNRPL  ALLDAESEDL  LLPLDEASWQ  SGIIHSNSPK
551    SDGPQCLLSA  DKNKRRLFPN  FICHDHSVFG  FFLPLMTITG  ELIDLNQARN
601    HPMLGMRLNG  KDAWNVHVSE  VLRQLEIYKA  SLTTFAATTS  DPEAPLSAYA
651    HAQSEHLPAE  PSLSQAYAWH  TQTVISYASY  LVHVLHILLV  GKWDPVSLIE
701    DKDFWTSSPA  FASTISHALD  AADSVDQILR  YDPDISFMPY  FFGIQLLQGS
751    FLLLLIVERL  QKEAGEGILN  ACEVMIRATE  SCVVTLNTEY  QRNFRQVMRS
801    AVAQARGRPV  NHSEIRHRRK  AVLALYRWTR  KGTGLAL*
```

Cysteines involved in a Zn2Cys6 cluster structure are marked in bold. The sequence underlined is included in an intron in the *A. nidulans* Annotated Database and, therefore, is missing in the annotated protein.

FIGURE 18A

SEQ ID NO:3 (A partial nucleotide sequence of the *pntR* gene from *A. niger*)

```
   1 tcttcgcagt gatatccggt gtgaattcac tcgcgaacga cgaaagagag gacgcattgc
  61 gcgatcccga ctggtagaga ccaagactgc tgtagagaag gcgagccagc ctgtggagac
 121 tcgagattca gcaccggcac ctgcagaagc agggtctggc ccagttccaa atggctctcc
 181 ttcctcaaca tttcaccata gatcgccggc gacaaatgat gtgacggggt cggccccaag
 241 tatcgacgag cggcgctctc aagcggatgt atcacttcct cccagaaagt cagggcacac
 301 tgttaatgcg acagaggaat ggctagcagg cacgcatgtc tctccaggat cctatgagcc
 361 cttggcaggc atcggccccg gagaaggccc tttccctcga atctttgata tctggaatgg
 421 ggtcgacttg gccggttata gcgacccagc atctcaaggc tccaagataa caggccttgg
 481 tcagacacca gcaccatctg caacgatcct aaagtatccg gtcctccagc cagtaatgcc
 541 ctatctggaa tcgagcttgc ctcgaaagct agtatacgac cttctcgacc tgtactttac
 601 aagcgcgttt tccacacata tgcatcctgt gtgccatcac attcattgct atgtcctacg
 661 aaaggcgtct tttctaagcc gagaggctcc tcgacctagc agcccggcac ttctggccag
 721 tatgctttgg gtggcagcgt tagatgatcg tgcgtttgct ttgccgatat ctccacccca
 781 gagaaagaaa atatgtcagt tcttgtgtgc tctaacatta cgactttgc gaccgttgat
 841 tcacgtgtca ttcaaagagc aagaaggcgc cgccgcgagt gacccacttc atgctgcggt
 901 cggtcaggat ggccctccta caaccgtgca ccacccgttt gaggtcggtg gtgatgatcg
 961 ggggttagtt ggccctgcag gatcattgga cgatgttatc acatacatcc atgtggcatc
1021 catcatctcc tcaagcgagc aaaaggccgc cagcatgcga tggttcgttt ttgttcaagt
1081 aacttgaggc gagcacggaa gctaaccaat cttaggtggc atgccgcctt tactcttgca
1141 cgagaattga agctgaatca ggagatcgag gtgatgccca gtgaggagaa tcacccagag
1201 ggttcgagcc cgtcatttga ttattcactt gcgggatgga gtggcgtgga cacgggcccc
1261 tttttgatt attcaaaccc tgcccggcca agcttgaatt gcgtatgcga ccgtggccac
1321 gaactgcgtg gcgctatcac cgaagagcat cgtgaagagc gtcgtcggac atggtggctc
1381 ctctacatta tggaccgtca cctcgctctc tgctacaatc gccccttgc tctactcgat
1441 gctgaaagcg aggatctctt attgcctctg gacgaagggt catggcagtc aggtaatatc
1501 cacagcaata gtcccaaccc ggacggacca cagtgcccac tgtcaggcga gaagaacaag
1561 cgccgcgttt tccctaattt catctgccat gatcattcta tcttcggctt ctttctccct
1621 ctgatgacca ttactggtga attaatcgac ctgaaccaag ctcggaacca tccaatgctt
1681 ggagcacgct tgaacggaaa ggacccctgg gatgcgcacg ttggtgaagt actacgccag
1741 cttgagcttt acaaggctag tctcactacg tttgcagcca ctgcgtcgga tcccgatgcg
1801 cccttgtcca gtgccttccc ccctaaaccc gatcaacaac cagttgaacc ctcactcgcc
1861 caggcttatt catggcatac tcaaacggtc atctcgtatg catcctacct cgtgcatgtg
1921 ctgcatattc ttcttgttgg caaatgggat cctgtgtcgt tgatcgagga taaggacttc
1981 tggacttcat cgcctgcatt cgcctccacc atctctcacg ctcttgatgc ggcagactca
```

FIGURE 18B

```
2041 gtggaccata tcttacgcta cgaccccgat attagtttta tgccgtattt cttcggcatt
2101 caattgctcc aaggcagctt tcttctcctg ctgattgtgg agcggctgca gaaagaagcg
2161 ggggagggta ttctaaatgc ctgcgaggtg atgattcgag cgaccgagtc ctgcgtggtg
2221 acgttgaaca ctgaatatca acggaacttc cgacaggtca tgcggagcgc cgttgcgcag
2281 gcgcgtgggc gccctgtcaa tcacagtgag atccggcatc gtngcaaggc cgtct
```

FIGURE 19

SEQ ID NO: 4 (The primary structure of the encoded transcription factor PntR)

| | | | | | |
|---|---|---|---|---|---|
| 1 | LRSDIRCEFT | RERRKRGRIA | RSRLVETKTA | VEKASQPVET | RDSAPAPAEA |
| 51 | GSGPVPNGSP | SSTFHHRSPA | TNDVTGSAPS | IDERRSQADV | SLPPRKSGHT |
| 101 | VNATEEWLAG | THVSPGSYEP | LAGIGPGEGP | FPRIFDIWNG | VDLAGYSDPA |
| 151 | SQGSKITGLG | QTPAPSATIL | KYPVLQPVMP | YLESSLPRKL | VYDLLDLYFT |
| 201 | SAFSTHMHPV | CHHIHCYVLR | KASFLSREAP | RPSSPALLAS | MLWVAALDDR |
| 251 | AFALPISPPQ | RKKICQFLCA | LTLRLLRPLI | HVSFKEQEGA | AASDPLHAAV |
| 301 | GQDGPPTTVH | HPFEVGGDDR | GLVGPAGSLD | DVITYIHVAS | IISSSEQKAA |
| 351 | SMRWWHAAFT | LARELKLNQE | IEVMPSEENH | PEGSSPSFDY | SLAGWSGVDT |
| 401 | GPFFDYSNPA | RPSLNCVCDR | GHELRGAITE | EHREERRRTW | WLLYIMDRHL |
| 451 | ALCYNRPLAL | LDAESEDLLL | PLDEGSWQSG | NIHSNSPNPD | GPQCPLSGEK |
| 501 | NKRRVFPNFI | CHDHSIFGFF | LPLMTITGEL | IDLNQARNHP | MLGARLNGKD |
| 551 | PWDAHVGEVL | RQLELYKASL | TTFAATASDP | DAPLSSAFPP | KPDQQPVEPS |
| 601 | LAQAYSWHTQ | TVISYASYLV | HVLHILLVGK | WDPVSLIEDK | DFWTSSPAFA |
| 651 | STISHALDAA | DSVDHILRYD | PDISFMPYFF | GIQLLQGSFL | LLLIVERLQK |
| 701 | EAGEGILNAC | EVMIRATESC | VVTLNTEYQR | NFRQVMRSAV | AQARGRPVNH |
| 751 | SEIRHRXKAV | | | | |

FIGURE 20A

SEQ ID NO: 5 (A nucleotide sequence of the *pntR* gene from *A. tubingensis* 4M-147) and its deduced primary structure.

```
   1 gcggcctatt agtgacaaac cagagtttgc caccagggca gtgaaccctg gagagctccc
  61 catgtgtggc ccggctctgg attagggccc ttttttagcg cgtgcggagt ccagccccga
 121 cggtttcccc gcgatggatc gcttctgctc tgcccggcct gttttgcgct ctgccactca
 181 gctcccttct tcctccatgg aaaagtcctc tcctctgctc tacggttttt tatccgcatt
 241 gcgtcttgtt aacggcgcat cctagaaggc ttagcggtcg tcgtgggtac gtatgtcaag
 301 ccagttactc atcaacaact gcctcggtct ctttccccgc ttgtaattgc ctggtaaggg
 361 ctaaggaccg gttctttcgc tcctttcgtc ttggccggtt gctgacttct caacccatt
 421 tttttcagac tgcgattctt ttgcataccc tcatatacct ctggaatcgc caatgtcggc
 481 ctgaaatgga tactgcccag tcggggacg cccaggcatc cagcgttcca gcagccaccg
 541 aagaaccaac cggcggagcc tcaacaaaac gtcgttggag aaggaatcgg atagcttgcg
 601 actcctgcca ttcgcgtcgc gtgcggtgcg atcgagcctt tccctgctcg cgctgccttc
 661 gcagtgaaat ccgatgcgag ttcactcggg aacgacgcaa gcgaggacgc attgcgcgat
 721 cccgactggt agagcccaat gctgccactg aaaagccgac caaacctgtg gagtcccaag
 781 ccgcagcacc ggcacctgcg gaagcaggat ctggtccggt tccaaatggc tctccctcta
 841 cgacttttcg ccatagatcg ccagcgacaa atgatgtgac ggtgtcagcc caagtattg
 901 acgagcggcg ctctcaggcg gatgtgtcac ttcctcccag gaagtcaggg catacagtta
 961 atgcgacaga ggaatggcta gcaggcacgc atgtctctcc aggttcctat gagcccttgg
1021 caggcatcgg ccctggggaa ggccttttc ctcggatctt tgatatctgg aatggggttg
1081 acctggccgg ttacagtgat ccagcatctc agggttccaa gataaccggc cttggacaga
1141 caccagcacc gtctgcaaca atcctaaaat atccagtact ccagccagta atgccatatt
1201 tggagtcgag cttgcctcga aagctagtat acgatcttct cgacctgtac ttcacaagcg
1261 cattctccac gcatatgcat cccgtgtgtc atcacatcca ctgctatgtt ctacgaaagg
1321 catcatttct gagccgggaa gcccctcggc ctagcagccc tgcacttctg gccagcatgc
1381 tttgggtggc agcgttagat gaccgtgcgt ttgctttgcc gatatctcct ccccagagga
1441 agaagatatg tcaattttta tgtgctctaa cgttacggct cttgcgaccg ttggttcacg
1501 tgtcattcaa agagcaagag ggcgccgcgg cgagcgaccc acttcatgct gcgatcggtc
1561 aggacggtcc ccctacaacg gtgcaccacc catttgaagc cggtggtgat gatcggggc
1621 tggtcggccc tgcaggatca ttggacgatg tcatcacata catccatgta gcatccatta
1681 tctcttcaag cgaacaaaag gccgccagca tgcgatggtt cgtttttattc aagttacccg
1741 aagcgagcaa ggaagctaac caatcttagg tggcatgccg cctttactct tgcacgggaa
1801 ctgaagctca atcaggagat cgaggtgatg cctagtgagg agaatcaccc agagggctcg
1861 agcccgtcat ttgattattc acttgcggga tggagtggcg ttgacacggg ccccttttc
```

FIGURE 20B

```
1921 gattattcaa accctgctcg gccaagcttg aattgcgtat gcgaccgtgg ccacgaattg
1981 cgtggcgcta ttaccgaaga gcaccgtgaa gagcgtcgtc ggacatggtg gcttctctac
2041 atcatggacc gtcacctcgc tctctgctac aatcgcccc ttgctctact cgatgctgaa
2101 agcgaggatc ttttattgcc gctggacgaa gggtcatggc agtctgggaa catccacagc
2161 aatagtccca aaccggatgg accacagtgc ccgctgtcag gcgagaagaa caaacgccgc
2221 gttttcccca atttcatttg ccatgaccac tctatcttcg gcttcttcct gcctctcatg
2281 accattactg gcgaattaat cgacttaaac caagctcgta accatccgat gcttggagca
2341 cgcttgaatg gaaaggacgc ctgggatgcg cacgtcggtg aagtgctgcg ccagcttgag
2401 ctttacaagg ctagtctcac aacgtttgct gccactgcgt cggatcccga tgcgcccta
2461 tccagtgcct ttcccctaa acccgatcag caaccagtcg agccctcact cgcccaggct
2521 tattcatggc atactcaaac ggtcatctcg tatgcatcct atcttgtgca tgtgctacat
2581 attcttcttg tcgggaaatg ggatcctgtg tcgttgatcg aagataagga cttctggact
2641 tcatcgcccg cgttcgcctc caccatctct cacgcccttg atgcggcaga ctcggtggac
2701 catatcctac gttacgaccc cgatatcagt tttatgccgt atttcttcgg catccaatta
2761 cttcaaggca gctttcttct cttgctgatt gtagagcggc tgcagaaaga agcggggggag
2821 ggtattctga atgcgtgcga ggtgatgatc cgagcgaccg agtcctgtgt ggtgacgttg
2881 aacactgaat accaacgaaa ctttcgacag gtcatgcgga gcgctgttgc gcaggcgcgt
2941 gggcgccctg tcaatcacag cgagatccgg catcgtcgca aggccgtctt agcactctac
3001 cggtggaccc ggaagggcac tgggttggcc ctttagattt agagtttctc acagcgccga
3061 tgcccatttc agcgcacggt tgcatcggct ccgcatccgc aggccatcgg ctggagagag
3121 cttaaatcat ctcccgccag ggcatgcttg gttctaggcc agtcgcagag actggcatat
3181 gcaggcacag tatcccctcc ctctcggttg attaccttgc ctgaacgggc tcgctccagc
3241 tcgcctctat ggctcattgc ccggtgcctg catctgccgg accttacccc ggcattggca
3301 attgatcgca acggctgctg ctattagccc aaagtatctc gtagtattta ttatttttt
3361 ttggatactg ctctccgatg ttaccctgta catatacgag catttatgct gttttggtg
3421 tctctggctt gtttgttctg actcgcgggt tttaatctac caaacggttt tttcttcttc
3481 tggacaccac ctcccgaatg ccatgcccct ttcctcctaa caaagcaaac atcgcttcta
3541 ggcatagacc gtcgctaaag tcgggcatcg catgattctg cacttggtgc aaggaccggg
3601 gttgttgggc ggccccttcc ccttacccca gatttaacga acgggccgtg ctcgctcggt
3661 ccgaacctgg gtctttcggt taaattctta aaaaccgaa gccgttgcgg ggagaaaagc
3721 cattgcattg gaatcgaac caacaggcgc tcagctttaa cagcctttaa ttcccgtagt
3781 tcggcaggcc ggggagggtg ctcggttaat tgccacacca gaatatgggg tatgcaaggt
3841 tcagcgacac cacatggncc ccgtgaagat cagatggttc ctggtccgtc aaatcactga
3901 gcttccctcg aggg
```

FIGURE 21

**SEQ ID NO: 6 (The deduced primary structure from the *pntR* gene from *A. tubingensis* 4M-147).**

| | | | | |
|---|---|---|---|---|
| 1 | MDTAQSGDAQ | ASSVPAATEE | PTGGASTKRR | WRRNRIACDS CHSRRVRCDR |
| 51 | AFPCSRCLRS | EIRCEFTRER | RKRGRIARSR | LVEPNAATEK PTKPVESQAA |
| 101 | APAPAEAGSG | PVPNGSPSTT | FRHRSPATND | VTVSAPSIDE RRSQADVSLP |
| 151 | PRKSGHTVNA | TEEWLAGTHV | SPGSYEPLAG | IGPGEGPFPR IFDIWNGVDL |
| 201 | AGYSDPASQG | SKITGLGQTP | APSATILKYP | VLQPVMPYLE SSLPRKLVYD |
| 251 | LLDLYFTSAF | STHMHPVCHH | IHCYVLRKAS | FLSREAPRPS SPALLASMLW |
| 301 | VAALDDRAFA | LPISPPQRKK | ICQFLCALTL | RLLRPLVHVS FKEQEGAAAS |
| 351 | DPLHAAIGQD | GPPTTVHHPF | EAGGDDRGLV | GPAGSLDDVI TYIHVASIIS |
| 401 | SSEQKAASMR | WWHAAFTLAR | ELKLNQEIEV | MPSEENHPEG SSPSFDYSLA |
| 451 | GWSGVDTGPF | FDYSNPARPS | LNCVCDRGHE | LRGAITEEHR EERRRTWWLL |
| 501 | YIMDRHLALC | YNRPLALLDA | ESEDLLLPLD | EGSWQSGNIH SNSPKPDGPQ |
| 551 | CPLSGEKNKR | RVFPNFICHD | HSIFGFFLPL | MTITGELIDL NQARNHPMLG |
| 601 | ARLNGKDAWD | AHVGEVLRQL | ELYKASLTTF | AATASDPDAP LSSAFPPKPD |
| 651 | QQPVEPSLAQ | AYSWHTQTVI | SYASYLVHVL | HILLVGKWDP VSLIEDKDFW |
| 701 | TSSPAFASTI | SHALDAADSV | DHILRYDPDI | SFMPYFFGIQ LLQGSFLLLL |
| 751 | IVERLQKEAG | EGILNACEVM | IRATESCVVT | LNTEYQRNFR QVMRSAVAQA |
| 801 | RGRPVNHSEI | RHRRKAVLAL | YRWTRKGTGL | AL |

Cysteines involved in a Zn2Cys6 cluster structure are marked in bold.

TRANSCRIPTION FACTORS

REFERENCE TO RELATED APPLICATIONS

This application is a continuation-in-part of International Patent Application No. PCT/IB2005/003600 filed Nov. 10, 2005 and published as WO 2006/051418 on May 18, 2006, which claims priority to Great Britain Patent Application No. 0424940.5 filed Nov. 11, 2004.

SEQUENCE LISTING

The instant application contains a Sequence Listing which has been submitted via EFS-Web and is hereby incorporated by reference in its entirety. Said ASCII copy, created on Jan. 22, 2010, is named 67450920.txt, and is 46,005 bytes in size.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attR1Buted to them in U.S. Patent law; e.g., they can mean "includes", "included", "including" and the like. Terms such as "consisting essentially of" and "consists essentially of" have the meaning attR1Buted to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascR1Bed to them in U.S. Patent law; namely, that these terms are closed ended.

FIELD OF THE INVENTION

The present invention relates to nucleic acid sequences encoding polypeptides of transcription factors and polypeptides encoded by the nucleic acid sequences.

The invention also relates to constructs, vectors, and host cells comprising the nucleic acid sequences.

Furthermore, the invention relates to processes involving modulating the production or function of the transcription factors and to host cells useful for the expression and production of proteins of interest, in which the production or function of the transcription factors has been modulated.

Additionally, the invention relates to methods for in vivo production of proteins of interest.

TECHNICAL BACKGROUND AND PRIOR ART

Filamentous fungi are known for their ability to produce a wide range of different metabolites and, in particular, secreted enzymes with various industrial applications including the provision of therapeutics or for use in the bakery industry.

Prior to development of fungal transformation systems, improvement of production strains was largely restricted to a strategy based on classical mutagenesis followed by screening for a phenotype or enzymatic activity desired and selection of the best producer strain.

Commercially, filamentous fungi have now become widely used host cell systems for the production of both homologous and heterologous proteins and to date, several molecular and genetic approaches have been successfully applied to optimise filamentous fungi, in particular those from the genus *Aspergilli*, as a cell factory.

In many cases, these approaches have led to elevated yields of both homologous and heterologous proteins, and substantially reduced the time required for implementation of a new production process at a large scale.

However, there remains a need for improved methods.

Filamentous fungi are well-known producers of cellulolytic and hemicellulolytic enzymes. The cellulase degradation system of these organisms consists of three classes of enzymes, endoglucanases, cellobiohydrolases and beta-glucosidases. Xylans are hemicellulose, heterogenous polymers, which require a more complex set of enzymes for their degradation. These enzymes, broadly classed as xylanases, include endoxylanase, beta-xylosidase, acetylxylan esterase, α-L-arabinofuranosidase, arabinoxylan arabinofuranohydrolase, beta glucuronidase, feruloyl esterase and p-coumaroyl esterase (Scheme 1).

The expression of cellulose- and xylan-degrading enzymes by *Aspergillus* and *Trichoderma* species is regulated at the transcriptional level. However, the mechanisms of repression and induction have not yet been completely elucidated.

The transcription factor xlnR was originally cloned from the filamentous fungus *A. niger* and identified as a transcriptional activator of xylanase-encoding genes (WO 97/00962). In fact, it has been shown to trigger the transcription of a broad set of genes involved in degradation of cellulose and hemicelluloses in a number of fungal species. Based on its structure, XlnR has been ascribed to a family of fungal transcription factors, whose DNA-binding domain is composed of 6 conserved cysteine residues chelating two Zn atoms, a so-called Zn binuclear cluster.

xlnR homologues have been cloned from various *Aspergilli* (*A. nidulans, A. oryzae, A. kawachii, A. tubingensis, A. flavus*), as well as from other fungi, like *Hepocrea jecorina* (anamorph: *T. reesei*). Moreover, similar sequences can be found in many publicly accessible fungal genome databases, such as *Aspergillus fumigatus, Neurospora crassa, Magnaporthe grisea, Podospora anserina, Fusarium gramenarium*. Though the overall homology between different species varies in the range of 50-90%, it exhibits nearly 100% identity within the DNA binding domain encompassing a cluster of six cysteine residues at the N-terminal part of the protein. In particular, a stretch of aa residues between the second and third cysteines represented by the sequence NQL-RTK (SEQ ID NO: 7) is extremely conserved. In general, this sequence determines the DNA-binding specificity of a $Zn_2Cys_6$ binuclear cluster protein, which, in the case of XlnR, recognises a cognate DNA target with the consensus core 5' GGCTAR 3' (de Vries and Visser, 2001; Microbiol Mol Biol Reviews v65: 497-522). Therefore, all these homologues could be predicted to play a role in transcriptional regulation of genes related to xylan degradation.

Lately, several approaches have been made to improve the production of proteins of interest (POIs) using recombinant host cells from filamentous fungi.

The most straightforward strategy for improving the yield of secreted homologous and heterologous proteins documented in the literature is to introduce multiple copies of a structural gene of interest (see, for example, Hessing et al, 1994). However, this may not always lead to overexpression of the gene of interest. The concentration of a protein of interest in the fungal cell has also been increased by expressing it from a strong promoter (Mathieu and Felenbok, 1994; Nikolaev et al., 2002; Rose and van Zyl, 2002).

Transcription of the xylanolytic and cellulolytic system and, as a consequence, the total enzyme production by *Aspergillus niger* could be enhanced by increasing the gene copy number of xlnR (Gielkens et al., 1999). Conversely, inactivation of xlnR by gene disruption leads to the loss of transcription of extracellular xylanolytic genes.

Another approach implies a modification of the promoter region of the gene of interest by mutating binding sites of a transcription factor. Promoter activity of the *Aspergillus oryzae* xynF1 gene, monitored by β-galactosidase activity, was successfully upregulated by mutating two non-canonical XlnR binding sites to a sequence, which is supposed to have the highest binding affinity (Marui et al., 2003). Transformants carrying three canonical XlnR binding sequences in the xynF1 promoter region produced 2.8 times more enzyme than those with the authentic promoter.

Many of the genes involved in carbon metabolism are subject to carbon repression mediated by the global repressor CreA. In fact, CreA controls gene expression at several levels and can repress both a structural and regulatory gene. Deletion or mutation of the CreA binding sites in the corresponding promoters results in partial derepression of transcription and improved protein production (Orejas et al., 1999). A further improvement was obtained in a creA derepressed background (Prathumpai et al., 2004).

In *Aspergilli*, D-xylose acts as the inducer of xylanolytic genes (de Vries et al, 1999; Gouka et al, 1996). In addition, xylanase production appeared to be improved in both *T. reesei* (Xiong et al, 2004) and *Penicillium canescens* (Vavilova et al., 2003) grown on L-arabinose-containing media.

Metabolic control analysis and metabolic pathway engineering are other helpful means of strain improvement. It has been shown that the flux control of xylose metabolism is exerted at the first two steps (Prathumpai et al., 2003). Disruption of one of the genes responsible for D-xylose reduction resulted in an increase of xylanase transcription (Hasper et al., 2000).

The most spectacular improvement of heterologous protein production yields was obtained by the C-terminal fusion of a protein of interest to a well-secreted fungal protein (Ward et al., 1990, Contreras et al., 1991).

In addition, deletion of genes with non-desirable activities, like proteases, appears to be extremely useful to elevate expression (Van den Hombergh et al., 1997).

It is an object of the present invention to provide improved methods for increasing production of proteins of interest in host cells in which the activity of a transcription factor involved in metabolic regulation has been modified.

SUMMARY OF THE INVENTION

The present invention relates to the identification of a novel transcription factor, PntR (stands for pentose regulator), which is a member of the Zn binuclear cluster family of fungal regulators. Cloning of the pntR genes from *A. nidulans, A. tubingensis* and *A. niger* is described herein and it is demonstrated that disruption of this gene impairs pentose, and, in particular, L-arabinose, metabolism resulting in elevated transcription of XlnR-regulated genes and down-regulation of L-arabinose-inducible genes. As a consequence, production of xylanases and β-glucanases has been improved several times followed by a slight decrease of α-arabinofuranosidase activity.

Without wishing to be bound by any particular theory it was experimentally observed that under certain conditions (in fungal strains with reduced metabolism of L-arabinose) L-arabinose or its intermediate metabolite, L-arabitol, can serve as efficient inducers of XlnR expression similar to D-xylose. Elevated levels of XlnR would result in increased expression of XlnR regulated genes.

Such strains with modulated metabolism can be considered as promising hosts for optimised heterologous expression driven from the XlnR-controlled promoters.

In a broad aspect, the present invention provides a method of expressing in a host cell a POI (protein of interest) whose coding sequence is under the transcriptional control of a promoter regulated by XlnR, said method comprising generating a knock down of the transcription factor PntR in said host cell. Such a method of expressing can be used in a production process for production of the POI.

In a broad aspect, the present invention further relates to organisms, such as microorganisms, and, in particular fungi, which have been modified to have a knock down of the transcription factor PntR so as to be capable of producing high levels of a POI whose coding sequence is under the transcriptional control of a promoter regulated by XlnR.

The present invention is advantageous as it provides an improved production process for the production of proteins of interest in filamentous fungi.

The transcription factor "PntR" refers in particular to a pntR gene or protein originating from a fungus and, preferably, a filamentous fungus. Thus, in a preferred embodiment, the nucleotide sequence encoding the PntR which is selected or targeted for knock down in the host cell of the present invention is a PntR sequence obtainable from (though it does not have to be actually obtained from) a fungus. In a particularly preferred embodiment, the fungus is selected from *Aspergillus nidulans, Aspergillus niger* and *Aspergillus tubingensis*.

Other suitable PntR genes from fungal species which can be targeted for knock down include those derived from other *Aspergilli* (*A. oryzae, A. kawachii, A. flavus* and *A. fumigatus*), as well as from other fungi, which include but is not limited to strains of *Cryctococcus, Filibasidium, Fusarium, Humicola, Magnaporthe, Mucor, Neurospora, Penicillium, Piromyces, Talaromyces, Thermoascus* and *Trichoderma*.

In another aspect, the present invention relates to an isolated and/or purified novel PntR polypeptide or functional fragment thereof wherein said PntR polypeptide is derivable from a fungal species. The invention also provides the nucleic acid sequence encoding said PntR polypeptide.

It is to be noted that the present invention provides an improved method for the in vivo production of proteins using a fungal production system. Such improved methods have hitherto not been disclosed or suggested in the art.

Aspects of the present invention are presented in the claims and in the following commentary.

For ease of reference, these and further aspects of the present invention are now discussed under appropriate section headings. However, the teachings under each section are not necessarily limited to each particular section.

As used with reference to the present invention, the terms "produce", "producing", "produced", "producible", "production" are synonymous with the respective terms "prepare", "preparing", "prepared", "preparation", "generated", "generation" and "preparable".

As used with reference to the present invention, the terms "expression", "expresses", "expressed" and "expressable" are synonymous with the respective terms "transcription", "transcribes", "transcribed" and "transcribable".

As used with reference to the present invention, the terms "transformation" and "transfection" refer to a method of introducing nucleic acid sequences into hosts, host cells, tissues or organs.

Other aspects concerning the nucleotide sequences which can be used in the present invention include: a construct comprising the sequences of the present invention; a vector comprising the sequences for use in the present invention; a plasmid comprising the sequences for use in the present invention; a transformed cell comprising the sequences for use in the present invention; a transformed tissue comprising the sequences for use in the present invention; a transformed organ comprising the sequences for use in the present invention; a transformed host comprising the sequences for use in the present invention; a transformed organism comprising the sequences for use in the present invention. The present invention also encompasses methods of expressing the nucleotide sequence for use in the present invention using the same, such as expression in a host cell; including methods for transferring same. The present invention further encompasses methods of isolating the nucleotide sequence, such as isolating from a host cell.

Other aspects concerning the amino acid sequences for use in the present invention include: a construct encoding the amino acid sequences for use in the present invention; a vector encoding the amino acid sequences for use in the present invention; a plasmid encoding the amino acid sequences for use in the present invention; a transformed cell expressing the amino acid sequences for use in the present invention; a transformed tissue expressing the amino acid sequences for use in the present invention; a transformed organ expressing the amino acid sequences for use in the present invention; a transformed host expressing the amino acid sequences for use in the present invention; a transformed organism expressing the amino acid sequences for use in the present invention. The present invention also encompasses methods of purifying the amino acid sequence for use in the present invention using the same, such as expression in a host cell; including methods of transferring same, and then purifying said sequence.

BRIEF DESCRIPTION OF THE DRAWINGS

FIG. 12A-12B. Alignment of PntR homologues from various *Apergillus* species. FIGS. 12A and 12B discloses SEQ ID NOS 32, 2, 4 and 6, respectively, in order of appearance.

FIGS. 16A-16B. Shows the coding sequence of the pntR gene From A. nidulans SEQ ID NO:1.

FIG. 17. Shows the deduced primary structure from the pntR gene from A. nidulans SEQ ID NO:2.

FIGS. 18A-18B. Shows a artial nucleotide sequence of the pntR gene from A. niger SEQ ID NO:3.

FIG. 19. Shows the primary structure of the encoded transcription factor PntR SEQ ID NO:4.

FIGS. 20A-20B. Shows a nucleotide sequence of the pntR gene from A. tubingensis 4M-147 and its deduced primary structure SEQ ID NO:5.

FIG. 21. Shows the deduced primary structure from the pntR gene from A. tubingensis 4M-147 SEQ ID NO:6.

DETAILED DISCLOSURE OF INVENTION

Figure 1:
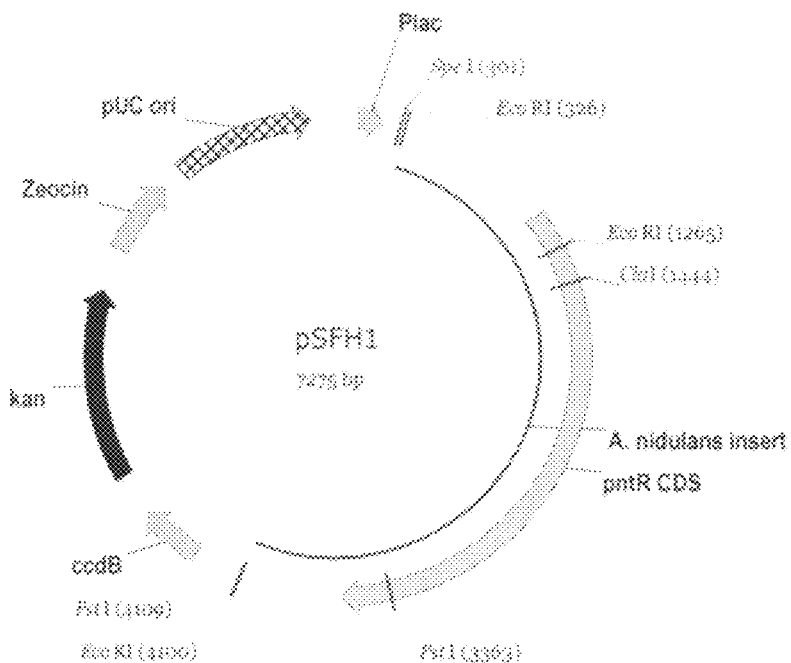
FIG. 1. A map of plasmid pSFH1.

In a first aspect, the present invention provides a method of expressing in a host cell of a protein of interest (POI) whose coding sequence is under the transcriptional control of a promoter regulated by XlnR, said method comprising generating a knock down of the transcription factor PntR in said host cell.

By the term "transcription factor" is meant polypeptide having transcription regulating activity.

Suitably the method provides increased expression of the POI i.e. an increased level of expression of the protein of interest compared with that obtained in a host cell that has not been modified in accordance with the invention.

XlnR regulates the transcription of a range of extracellular carbohydrate hydrolysing enzymes including the main xylanolytic enzymes. Accordingly, in one embodiment of the invention, the protein of interest (POI) may be encoded by a natural XlnR-regulated gene. Natural XlnR-regulated genes in *Aspergilli* include, for example, xlnA, B, C, D, xyrA, eglA, B, C, axhA, axeA, aguA, faeA, cbhA, B and aglB (de Vries and Visser, 2001). In another embodiment, the POI is a heterologous protein.

By the term homologous protein we understand a POI whose coding sequence is natively under the transcriptional control of a promoter regulated by XlnR in a parent cell of the host cell.

By the term heterologous protein we understand a POI whose coding sequence is not natively under the transcriptional control of a promoter regulated by XlnR in a parent cell of the host cell. Examples of such POIs include proteins not controlled by XlnR regulated promoters in the parent cell or proteins derived from organisms other than the parent cell of the host.

Suitably, the POI is a xylanolytic enzyme such as xylanase or endoglucanase. In a preferred embodiment of the present invention, the POI is a heterologous protein. Such POIs of interest include, but are not restricted to, amylases, oxidoreductases, lipases, phytases, pectinolytic or pectin modifying enzymes.

Examples of promoters regulated by XlnR are the promoters of xylanase A, xlnA, and endoglucanase A, eglA, from *Aspergillus tubingensis*. The sequence of the xlnA promoter, for example, is described by de Graaff et al, 1994 (Mol. Microbiol, v12: 479-490).

The transcription factor PntR is identified herein for the first time. PntR is a member of the Zn binuclear cluster family of fungal regulators. While the present application describes gene sequences for PntR in *Aspergillus* which are set out in SEQ ID NOS: 1, 3 and 5, the method of the invention also incorporates knock down of PntR corresponding to or homologous to *Aspergillus* PntR. The term "corresponding to *Aspergillus* PntR" means that the transcription factor has the same sequence as that of an *Aspergillus* PntR or has a sequence that is more than 60% identical to that of *Aspergillus* PntR. The method further incorporates knock down of PntR homologues in other species of fungi and, in particular, other species of filamentous fungi.

In a preferred embodiment, the transcription factor PntR comprises an amino acid sequence as set out in any of SEQ ID NOS: 2, 4 or 6.

By "modulating the transcription factor PntR" or "disrupting PntR expression" is meant modifying and, in particular reducing, PntR expression or activity to generate a reduced level or zero level of the transcription factor. In particular, modifying, modulating, disrupting or knock down of PntR refers to knock out techniques for the elimination or reduction of expression of a specific gene sequence through recombinant techniques. Such techniques are well known to those skilled in the art and include techniques to generate loss of function of a selected gene through gene silencing techniques such as homologous recombination, gene disruption, antisense and siRNA techniques. Suitable techniques are described in the Examples section.

Modulating further relates to the knock down of transcription factor function at the protein level through techniques such as dominant negative protein expression methodologies. Such techniques will be familiar to those skilled in the art. For example, transcription factor function may be modulated through the introduction of a nucleic acid sequence encoding a functionally disrupted PntR such as a nucleic acid sequence encoding PntR and lacking the region encoding $Zn_2Cy_6$.

Suitable host cells include filamentous fungal cells including *Aspergillus*, *Trichoderma* and *Penicillium* spp. Other suitable host cells include basidiomycetes, yeast and bacteria.

In one embodiment, said method further comprises isolating/purifying said POI.

In another aspect of the invention, there is provided a PntR transcription factor. Suitably said transcription factor comprises the amino acid sequence corresponding to *Aspergillus* PntR or a functional equivalent thereof.

By "*Aspergillus* PntR" is meant PntR from an *Aspergillus* species. In particular, *Aspergillus* PntR refers to PntR from *Aspergillus nidulans, Aspergillus niger* and *Aspergillus tubingensis*. Other *Aspergillus* species include *Aspergillus oryzae, Aspergillus kawachii, Aspergillus fumigatus* and *Aspergillus flavus*.

Other suitable PntR genes from fungal species which can be targeted for knock down include those derived from other fungi, which include but is not limited to strains of *Cryptococcus, Filibasidium, Fusarium, Humicola, Magnaporthe, Mucor, Neurospora, Penicillium, Piromyces, Talaromyces, Thermoascus* and *Trichoderma*.

The term "functional equivalent thereof" means that the transcription factor has the same functional characteristics as that of *Aspergillus* PntR.

Preferably the transcription factor of this aspect of the present invention has the same amino acid sequence or a sequence that is at least 75% identical (homologous) to that of *Aspergillus* PntR.

Suitably, the transcription factor comprises the amino acid sequence as shown in any of SEQ ID NOs: 2, 4 or 6 or a sequence having at least 75% identity (homology) thereto or an effective fragment thereof. In a preferred embodiment, the invention provides an isolated and/or purified polypeptide having the amino acid sequence as set out in any of SEQ ID NOs: 2, 4 or 6 or a sequence having at least 75% identity (homology) thereto or an effective fragment thereof.

In another aspect, the invention provides an isolated and/or purified nucleic acid molecule, nucleic acid or nucleotide sequence coding for the PntR transcription factor of *Aspergillus* PntR, or a homologue thereof. Suitably said isolated and/or purified nucleic acid molecule encodes a polypeptide comprising the amino acid sequence as shown in any of SEQ ID NOs: 2, 4 or 6 or a sequence having at least 75% identity (homology) thereto or an effective fragment thereof. In another embodiment, the invention provides an isolated and/or purified nucleic acid molecule or sequence comprising a nucleotide sequence that is the same as, or is complementary to, or contains any suitable codon substitutions for any of those of any of SEQ ID NOs: 1, 3 or 5 or comprises a sequence which has at least 60%, 65%, 75%, 80%, 85%, 90%, 95% or 99% sequence homology with any of SEQ ID NOs: 1, 3 or 5.

In a yet further aspect, the invention relates to a nucleotide sequence and to the use of a nucleotide sequence shown as:
(a) the nucleotide sequence presented as any of SEQ ID Nos. 1, 3 or 5,
(b) a nucleotide sequence that is a variant, homologue, derivative or fragment of the nucleotide sequence presented as any of SEQ ID Nos. 1, 3 or 5;

(c) a nucleotide sequence that is the complement of the nucleotide sequence set out in any of SEQ ID Nos. 1, 3 or 5;
(d) a nucleotide sequence that is the complement of a variant, homologue, derivative or fragment of the nucleotide sequence presented as any of SEQ ID Nos 1, 3 or 5;
(e) a nucleotide sequence that is capable of hybridising to the nucleotide sequence set out in any of SEQ ID Nos. 1, 3 or 5;
(f) a nucleotide sequence that is capable of hybridising to a variant, homologue, derivative or fragment of the nucleotide sequence presented as any of SEQ ID Nos. 1, 3 or 5;
(g) a nucleotide sequence that is the complement of a nucleotide sequence that is capable of hybridising to the nucleotide sequence set out in any of SEQ ID Nos. 1, 3 or 5;
(h) a nucleotide sequence that is the complement of a nucleotide sequence that is capable of hybridising to a variant, homologue, derivative or fragment of the nucleotide sequence presented as any of SEQ ID Nos. 1, 3 or 5;
(i) a nucleotide sequence that is capable of hybridising to the complement of the nucleotide sequence set out in any of SEQ ID Nos. 1, 3 or 5;
(j) a nucleotide sequence that is capable of hybridising to the complement of a variant, homologue, derivative or fragment of the nucleotide sequence presented as any of SEQ ID Nos. 1, 3 or 5.

The nucleotide sequences of the present invention may comprise sequences that encode for any of SEQ ID Nos. 2, 4 or 6 or a variant, homologue or derivative thereof.

The nucleotide sequences of the present invention may be useful in generating corresponding sequences for use in the knock down of PntR expression in a cell for use in accordance with the method of the invention. In particular, the nucleotide sequences of the present invention may be used for identifying siRNA molecules or antisense molecules which can be used to knock down PntR expression. In addition, the nucleotide sequences of the present invention may be useful if identifying flanking regions outside the pntR gene which can be used for generating pntR knockouts through techniques such as homologous recombination. These and other suitable methods will be familiar to those skilled in the art.

The invention also provides a plasmid or vector system comprising a PntR as described herein or a homologue or derivative thereof. Preferably, the plasmid or vector system comprises a nucleic acid sequence as set out in any of SEQ ID Nos 1, 3 or 5 or a sequence that is at least 75% homologous thereto or an effective fragment thereof. Suitably the plasmid or vector system is an expression vector for the expression of any of a transcription factor encoded by a nucleic acid sequence as set out in any of SEQ ID Nos: 1, 3 or 5 or a sequence that is at least 75% homologous (identical) thereto in a microorganism. Suitable expression vectors are described herein.

In one aspect of the invention there is provided a host cell transformed or transfected with a nucleic acid in accordance with any aspect of the invention.

In another aspect of the invention, there is provided an isolated nucleic acid molecule arranged to knock down the expression or function of the transcription factor PntR. Suitable nucleic acid molecules include those comprising a disrupted PntR coding region for use in a homologous recombination approach. Methods for generating such constructs will be familiar to those skilled in the art. One suitable method and construct is exemplified herein. Other suitable nucleic acid molecules include siRNA molecules and antisense constructs.

In a further aspect of the invention there is provided a host cell transformed or transfected with a nucleic acid construct arranged to knock down the expression or function of the transcription factor PntR. Suitably, the PntR is an *Aspergillus* PntR as described herein or a homologue or derivative thereof. In one embodiment said nucleic acid construct comprises a disrupted PntR coding region for use in a homologous recombination approach.

Suitably, said host cell further comprises a nucleic acid construct comprising a coding sequence of a protein of interest (POI) under the transcriptional control of a promoter regulated by XlnR.

In a preferred embodiment, the host cell is a microorganism including fungi. Suitable fungal host cells include filamentous fungi including those selected from the group consisting of *Aspergillus, Trichoderma* and *Penicillium*.

In one embodiment, the host cell in accordance with this aspect of the invention has a block in L-arabinose metabolism.

By a "block in L-arabinose metabolism" is meant that the host cell transformed or transfected with a nucleic acid construct arranged to knock down the expression or function of the transcription factor PntR has a lower level of L-arabinose metabolism compared to an unmodified cell. Suitable methods for detecting a block in L-arabinose metabolism are described herein.

In another embodiment, the host cell in accordance with this aspect of the invention exhibits increased xylanase activity.

By "increased xylanase activity" is meant that the host cell transformed or transfected with a nucleic acid construct arranged to knock down the expression or function of the transcription factor PntR has a higher level of xylanase compared to an unmodified cell. Suitable methods for measuring said activity are described herein.

In another embodiment, the host cell may comprise an additional modification such as, for example, the host cell may have a protease deficient background.

In a further aspect of the invention there is provided use of the modulation of the transcription factor PntR in the manufacture of a host cell to increase expression of a protein of interest (POI) whose coding sequence is under the transcriptional control of a promoter regulated by XlnR.

Preferable Aspects

Preferable aspects are presented in the accompanying claims and in the following description and Examples section.

Additional Advantages

The present invention is advantageous as it provides an improved microbiological process for the synthesis of a variety of proteins of interest and, in particular, for the synthesis of extracellular xylanases.

Disruption of PntR in both *A. nidulans* and *A. tubingensis* strains impairs L-arabinose metabolism resulting in elevated transcription of XlnR-regulated genes and down-regulation of L-arabinose-inducible genes. As a consequence, production of xylanases and β-glucanases has been improved several times followed by a slight decrease of α-arabinofuranosidase activity. Such strains with modulated metabolism can be considered as promising hosts for optimised heterologous expression driven from the XlnR-controlled promoters.

The xylanases which are produced using this improved microbiological process are useful in various applications in the food industry—such as in bakery and drink products, they may also be used in other applications such as for feed production or even in the paper or textile industry for paper and tissue bleaching.

As described herein, the knockout (deletion or disruption or any loss-of-function mutation) of PntR results in significant (3-5 fold) increase of XlnR-controlled genes including xylanase, β-glucanase, β-xylosidase either on industrially relevant complex media with sugar beet pulp or in the presence of L-arabinose or L-arabitol.

The present method enables improved xylanase production and also improved heterologous protein expression in general.

High levels of proteases in filamentous fungi often limits the expression of homologous and heterologous proteins at high levels. By using protease deficient strains, protein production in *Aspergilli* can be improved considerably. Both classical and gene disruption techniques have resulted in strains with a reduced protease background. Further improvements of product yields were observed under conditions that repress the expression of several proteases (Van den Hombergh et al., 1997). In the present invention, optimal expression conditions may be those when a carbon source provided is limited where, advantageously, a pntR knockout may be combined with a protease deficient background.

Isolated

In one aspect, preferably the sequence is in an isolated form. The term "isolated" means that the sequence is at least substantially free from at least one other component with which the sequence is naturally associated in nature and as found in nature.

Purified

In one aspect, preferably the sequence is in a purified form. The term "purified" means that the sequence is in a relatively pure state—e.g. at least about 90% pure, or at least about 95% pure or at least about 98% pure.

Nucleotide Sequence

The scope of the present invention encompasses nucleotide sequences encoding transcription factors having the specific properties as defined herein.

The term "nucleotide sequence" as used herein refers to an oligonucleotide sequence, nucleic acid or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" or "nucleic acid molecule" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Preparation of a Nucleotide Sequence

Typically, the nucleotide sequence encompassed by scope of the present invention or the nucleotide sequences for use in the present invention are prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

A nucleotide sequence encoding either a transcription factor which has the specific properties as defined herein or a transcription factor which is suitable for modification may be identified and/or isolated and/or purified from any cell or organism expressing said transcription factor. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the transcription factor. If the amino acid sequence of the transcription factor or a part of the amino acid sequence of the transcription factor is known, labelled oligonucleotide probes may be synthesised and used to identify transcription factor-encoding clones from the genomic library prepared from the organism. Alternatively, a labelled oligonucleotide probe containing sequences homologous to another known transcription factor gene could be used to identify transcription factor-encoding clones. In the latter case, hybridisation and washing conditions of lower stringency are used.

In a yet further alternative, the nucleotide sequence encoding the transcription factor or the nucleotide sequence for use in the method of the invention may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science*(1988) 239, pp 487-491).

Due to degeneracy in the genetic code, nucleotide sequences may be readily produced in which the triplet codon usage, for some or all of the amino acids encoded by the original nucleotide sequence, has been changed thereby producing a nucleotide sequence with low homology to the original nucleotide sequence but which encodes the same, or a variant, amino acid sequence as encoded by the original nucleotide sequence. For example, for most amino acids the degeneracy of the genetic code is at the third position in the triplet codon (wobble position) (for reference see Stryer, Lubert, Biochemistry, Third Edition, Freeman Press, ISBN 0-7167-1920-7) therefore, a nucleotide sequence in which all triplet codons have been "wobbled" in the third position would be about 66% identical to the original nucleotide sequence however, the amended nucleotide sequence would encode for the same, or a variant, primary amino acid sequence as the original nucleotide sequence.

Therefore, the present invention further relates to any nucleotide sequence that has alternative triplet codon usage for at least one amino acid encoding triplet codon, but which encodes the same, or a variant, polypeptide sequence as the polypeptide sequence encoded by the original nucleotide sequence.

Furthermore, specific organisms typically have a bias as to which triplet codons are used to encode amino acids. Preferred codon usage tables are widely available, and can be used to prepare codon optimised genes. Such codon optimisation techniques are routinely used to optimise expression of transgenes in a heterologous host.

Molecular Evolution

Once a transcription factor-encoding nucleotide sequence has been isolated and/or purified, or a putative transcription factor-encoding nucleotide sequence has been identified, the selected nucleotide sequence may be modified in order to generate a gene disruption or loss of function mutant. For example, it may be desirable to mutate the sequence in order to prepare a dominant negative transcription factor or alternative loss of function mutant.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into transcription factor-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence.

Thus, it is possible to produce numerous site directed or random mutations into a nucleotide sequence, either in vivo or in vitro, and to subsequently screen for the desired functionality of the encoded polypeptide by various means.

Amino Acid Sequences

The scope of the present invention also encompasses amino acid sequences of transcription factors having the specific properties as defined herein. There is also provided amino acid sequences based on the transcription factors identified herein but generated or modified so as to provide a knock down of the expressed PntR by methods such as a dominant negative approach.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme" or "transcription factor".

The amino acid sequence may be prepared/isolated from a suitable source, or it may be made synthetically or it may be prepared by use of recombinant DNA techniques.

Preferably the amino acid sequence when relating to and when encompassed by the per se scope of the present invention is not a native transcription factor. In this regard, the term "native transcription factor" means an entire transcription factor that is in its native environment and when it has been expressed by its native nucleotide sequence.

Variants/Homologues/Derivatives

The present invention also encompasses the use of variants, homologues and derivatives of any amino acid sequence of a transcription factor or of any nucleotide sequence encoding such a transcription factor.

Here, the term "homologue" means an entity having a certain homology with the amino acid sequences and the nucleotide sequences. Here, the term "homology" can be equated with "identity".

In the present context, a homologous amino acid sequence is taken to include an amino acid sequence which may be at least 75, 80, 81, 85 or 90% identical, preferably at least 95, 96, 97, 98 or 99% identical to the sequence. Typically, the homologues will comprise the same functional regions etc.—e.g as the subject amino acid sequence. In particular, it is preferred that homologues comprise the functional domains which are necessary for transcription factor activity including, for example, those domains necessary for DNA recognition and interaction with transcriptional machinery. Although homology can also be considered in terms of similarity (i.e. amino acid residues having similar chemical properties/functions), in the context of the present invention it is preferred to express homology in terms of sequence identity.

By "functional fragment" is meant a fragment of the polypeptide that retains the characteristic properties of that polypeptide. In the context of the present invention, a functional fragment of a PntR transcription factor is a fragment that retains the activator capability of the whole protein.

In the present context, an homologous nucleotide sequence is taken to include a nucleotide sequence which may be at least 60, 65, 75, 80, 81, 85 or 90% identical, preferably at least 95, 96, 97, 98 or 99% identical to a nucleotide sequence encoding an transcription factor of the present invention (the subject sequence). Typically, the homologues will comprise the same sequences that code for the functional sites etc. as the subject sequence. Although homology can also be considered in terms of similarity (i.e. amino acid residues having similar chemical properties/functions), in the context of the present invention it is preferred to express homology in terms of sequence identity.

For the amino acid sequences and the nucleotide sequences, homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999 *Short Protocols in Molecular Biology*, 4$^{th}$ Ed—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60).

However, for some applications, it is preferred to use the GCG Bestfit program. A new tool, called BLAST 2 Sequences is also available for comparing protein and nucleotide sequence (see *FEMS Microbiol Lett* 1999 174(2): 247-50; *FEMS Microbiol Lett* 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" *Comput. Appl Biosci.* 9: 745-756)(Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| SET | | SUB-SET | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alamine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Biologically Active

Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein.

More preferably, the term "variant" encompasses sequences that are complementary to sequences that are capable of hybridising under high stringent conditions (e.g. 65° C. and 0.1×SSC {1×SSC=0.15 M NaCl, 0.015 M Na$_3$citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 50° C. and 0.2×SSC).

In a more preferred aspect, the present invention covers nucleotide sequences that can hybridise to the nucleotide sequence of the present invention, or the complement thereof, under high stringent conditions (e.g. 65° C. and 0.1×SSC).

Methods for Modulating Protein Expression or Function

The functional activity of a PntR transcription factor may be modified by suitable molecules/agents which bind either directly or indirectly to the PntR protein, or to the nucleic acid encoding it. Agents may be naturally occurring molecules such as peptides and proteins, for example specific activating protein kinases, or they may be metabolites, like sugars or polyols or their derivatives, or they may be synthetic molecules.

Methods of modulating the level of expression of a PntR transcription factor protein include, for example, using antisense techniques.

Antisense constructs, i.e., nucleic acid, preferably RNA, constructs complementary to the sense nucleic acid or mRNA, are described in detail in U.S. Pat. No. 6,100,090 (Monia et al.), and Neckers et al., 1992, *Crit. Rev Oncog* 3(1-2):175-231, the teachings of which document are specifically incorporated by reference. Other methods of modulating gene expression are known to those skilled in the art and include dominant negative approaches as well as introducing peptides or small molecules which inhibit gene expression or functional activity.

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., *Nature* 391:806-811 (1998). Other methods of PTGS are known and include, for example, introduction of a transgene or virus. Generally, in PTGS, the transcript of the silenced gene is synthesised but does not accumulate because it is rapidly degraded. Methods for PTGS, including RNAi are described, for example, in the Ambion.com world wide web site, in the directory "/hottopics/", in the "rnai" file.

Suitable methods for RNAi in vitro are known to those skilled in the art. One such method involves the introduction of siRNA (small interfering RNA). Current models indicate that these 21-23 nucleotide dsRNAs can induce PTGS. Methods for designing effective siRNAs are described, for example, in the Ambion web site described above.

Site-Directed Mutagenesis

Once a PntR transcription factor-encoding nucleotide sequence has been isolated and/or purified, or a putative transcription factor-encoding nucleotide sequence has been identified, it may be desirable to mutate the sequence. For example, a disrupted PntR sequence may be introduced into the cell to disrupt the endogenous PntR gene through homologous recombination. Suitable constructs are described herein. Alternatively, the PntR sequence may be mutated in order to prepare a dominant negative protein that interrupts the function or expression of naturally expressed PntR.

Mutations may be introduced using synthetic oligonucleotides. These oligonucleotides contain nucleotide sequences flanking the desired mutation sites.

A suitable method is disclosed in Morinaga et al., (*Biotechnology* (1984) 2, p 646-649). Another method that may be applicable to introducing mutations into transcription factor-encoding nucleotide sequences is described in Nelson and Long (*Analytical Biochemistry* (1989), 180, p 147-151). A further method is described in Sarkar and Sommer (*Biotechniques* (1990), 8, p 404-407—"The megaprimer method of site directed mutagenesis").

Recombinant

In one aspect the sequence for use in the present invention is a recombinant sequence—i.e. a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

Synthetic

In one aspect the sequence for use in the present invention is a synthetic sequence—i.e. a sequence that has been prepared by in vitro chemical or enzymatic synthesis. It includes, but is not limited to, sequences made with optimal codon usage for host organisms.

Expression of Proteins

The nucleotide sequence for use in the present invention may be incorporated into a recombinant replicable vector. The vector may be used to replicate and express the nucleotide sequence, in enzyme form, in and/or from a compatible host cell.

Expression may be controlled using control sequences eg. regulatory sequences.

Expression Vector

The terms "plasmid", "vector system" or "expression vector" means a construct capable of in vivo or in vitro expression. In the context of the present invention, these constructs may be used to introduce genes encoding transcription factors into host cells. Suitably, the genes whose expression is introduced may be referred to as "expressible transgenes".

In another embodiment, these constructs may be used to introduce a gene encoding a protein of interest under the control of an XlnR promoter sequence into host cells.

Preferably, the expression vector is incorporated into the genome of a suitable host organism. The term "incorporated" preferably covers stable incorporation into the genome.

The nucleotide sequences described herein including the nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector eg. a plasmid, cosmid, or phage vector will often depend on the host cell into which it is to be introduced.

The vectors for use in the present invention may contain one or more selectable marker genes-such as a gene, which confers antibiotic resistance eg. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

Suitably, for expression of a POI, the gene encoding the POI is operably linked to a promoter sequence which enables that sequence to be under transcriptional control of a promoter regulated by XlnR. Suitable said promoter sequence could be the xlnA or eglA promoter sequence.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the POI in accordance with the present invention may also be achieved by the selection of additional heterologous regulatory regions, e.g. promoter, secretion leader and terminator regions.

Preferably, the nucleotide sequence according to the present invention is operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence for use according to the present invention. Such a construct may be directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any cell that comprises either the nucleotide sequence or an expression vector as described above and which is used in the recombinant production of a transcription factor having the specific properties as defined herein or in the methods of the present invention.

Thus, a further embodiment of the present invention provides host cells transformed or transfected with a nucleotide sequence that expresses the transcription factors described in the present invention. The cells will be chosen to be compatible with the said vector and may for example be prokaryotic (for example bacterial), fungal, yeast or plant cells. Preferably, the host cells are not human cells.

In another embodiment, the invention provides a host cell generated by the method of the invention i.e. comprising a gene encoding a POI operably linked under the transcriptional control of a promoter regulated by XlnR wherein said host cell further comprises a knock down in expression or activity of PntR.

Examples of suitable host organisms are fungal cells including filamentous fungi.

The host cell may be a protease deficient or protease minus strain, such as pep- or prt protease deficient strains in *Aspergilli* (van den Hombergh, 1997, Curr Genet July; 32(1): 73-81).

The genotype of the host cell may be modified to improve expression.

Examples of host cell modifications include protease deficiency, carbon catabolite derepression, supplementation of rare tRNA's, and modification of the reductive potential in the cytoplasm to enhance disulphide bond formation.

Organism

The term "organism" in relation to the present invention includes any organism that could comprise the nucleotide sequence coding for the transcription factors as described in the present invention and/or products obtained therefrom, and/or wherein a promoter can allow expression of the nucleotide sequence according to the present invention when present in the organism. In addition the term organism extends to an organism generated in accordance with the method of the invention i.e. modified to express a POI at increased levels.

Suitable organisms may include a fungus. Other suitable organisms may include yeast or plant cells.

The term "transgenic organism" in relation to the present invention includes any organism that comprises the nucleotide sequence coding for the transcription factors as described in the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the transcription factors as described in the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the transcription factor of the present invention under the control of a heterologous promoter.

Transformation of Host Cells/Organism

As indicated earlier, the host organism can be a eukaryotic organism and, in particular a fungus. Particularly preferred are filamentous fungus. Examples of suitable such hosts include any member belonging to the genera *Thermomyces, Acremonium, Aspergillus, Penicillium, Mucor, Neurospora, Trichoderma* and the like.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023. Teachings on transforming filamentous fungi are also reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143. Further teachings on transforming filamentous fungi are reviewed in U.S. Pat. No. 5,674,707.

In one aspect, the host organism can be of the genus *Aspergillus*, such as *Aspergillus niger*.

Suitable markers for transformation in fungi include but is not restricted to the resistance genes encoding ornithine carbamoyltransferase, argB, and orotidine-5'-monophosphate decarboxylase, pyrG.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus*: 50 years on. Progress in industrial microbiology vol 29. Elsevier Amsterdam 1994. pp. 641-666). Filamentous fungi can be also transformed using *Agrobacterium tumefaciens*-mediated transformation (Gouka et al, 1999, Nat. Biotech). Gene expression in filamentous fungi has been reviewed in Punt et al. (2002) Trends Biotechnol 2002 May; 20(5):200-6, Archer & Peberdy Crit. Rev Biotechnol (1997) 17(4):273-306.

Culturing and Production

Host cells transformed with the nucleotide sequence of the present invention may be cultured under conditions conducive to the production of a POI and which facilitate recovery of the POI from the cells and/or culture medium.

Accordingly, the invention provides a method of expressing a POI which may be part of a method of production of said POI and further comprise isolating and/or purifying said POI.

The medium used to cultivate the cells may be any conventional medium suitable for growing the host cell in question and obtaining expression of the enzyme.

The protein produced by a recombinant cell may be displayed on the surface of the cell.

The POI may be secreted from the host cells and may conveniently be recovered from the culture medium using well-known procedures.

Secretion

It may be desirable for the POI to be secreted from the expression host into the culture medium from where the POI may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the α-factor gene (yeasts e.g. *Saccharomyces*, *Kluyveromyces* and *Hansenula*) or the α-amylase gene (*Bacillus*).

By way of example, the secretion of heterologous proteins in *E. coli* is reviewed in *Methods Enzymol* (1990) 182:132-43.

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

Fusion Proteins

The amino acid sequences for use according to the present invention as well as the POI produced in accordance with the invention may be produced as fusion proteins, for example to aid in extraction and purification. Examples of fusion protein partners include glutathione-S-transferase (GST), 6×His (SEQ ID NO: 33), GAL4 (DNA binding and/or transcriptional activation domains) and (β-galactosidase). It may also be convenient to include a proteolytic cleavage site between the fusion protein partner and the protein sequence of interest to allow removal of fusion protein sequences.

Preferably, the fusion protein will not hinder the activity of the protein sequence although in one embodiment a dominant negative transcription factor approach is preferred.

Gene fusion expression systems in *E. coli* have been reviewed in *Curr Opin Biotechnol* (1995) 6(5):501-6.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

In one embodiment of the present invention the C-terminal of a POI is fused to, for example a well-secreted fungal protein, such as a glucoamylase, xylanase or endoglucanase or parts thereof for improved heterologous protein production yield.

PntR may also be modified in a dominant negative approach using a peptide library, for example.

Additional Sequences

The sequences for use according to the present invention may also be used in conjunction with one or more additional proteins of interest (POIs) or nucleotide sequences of interest (NOIs).

Non-limiting examples of POIs include: proteins or enzymes involved in xylan or cellulose metabolism or combinations thereof. Other suitable POIs include but is not restricted to phytase, lipase, amylase or mammalian proteins of interest, such as human antibodies, tissue plasminogen activator and interleukins. The NOI may even be an antisense sequence for any of those sequences.

Other sequences can also facilitate secretion or increase the yield of secreted POI. Such sequences could code for chaperone proteins as for example the product of *Aspergillus niger* cyp B gene described in UK patent application 9821198.0.

The NOI coding for POI may be engineered in order to alter their activity for a number of reasons, including but not limited to, alterations, which modify the processing and/or expression of the expression product thereof. By way of further example, the NOI may also be modified to optimise expression in a particular host cell. Other sequence changes may be desired in order to introduce restriction enzyme recognition sites.

The NOI coding for the POI may include within it synthetic or modified nucleotides—such as methylphosphonate and phosphorothioate backbones.

The NOI coding for the POI may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

Antibodies

One aspect of the present invention relates to amino acids that are immunologically reactive with the amino acid of any of SEQ ID Nos. 2, 4 or 6.

Antibodies may be produced by standard techniques, such as by immunisation with the substance of the invention or by using a phage display library.

For the purposes of this invention, the term "antibody", unless specified to the contrary, includes but is not limited to, polyclonal, monoclonal, chimeric, single chain, Fab fragments, fragments produced by a Fab expression library, as well as mimetics thereof. Such fragments include fragments of whole antibodies which retain their binding activity for a target substance, Fv, F(ab') and F(ab')$_2$ fragments, as well as single chain antibodies (scFv), fusion proteins and other synthetic proteins which comprise the antigen-binding site of the antibody. Furthermore, the antibodies and fragments thereof may be humanised antibodies. Neutralising antibodies, i.e., those which inhibit biological activity of the substance polypeptides, are especially preferred for diagnostics and therapeutics.

If polyclonal antibodies are desired, a selected mammal (e.g., mouse, rabbit, goat, horse, etc.) is immunised with the sequence of the present invention (or a sequence comprising an immunological epitope thereof). Depending on the host species, various adjuvants may be used to increase immunological response.

Serum from the immunised animal is collected and treated according to known procedures. If serum containing polyclonal antibodies to the sequence of the present invention (or a sequence comprising an immunological epitope thereof) contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against the sequence of the present invention (or a sequence comprising an immunological epitope thereof) can also be readily produced by one skilled in the art and include, but are not limited to, the hybridoma technique Koehler and Milstein (1975 *Nature* 256:495-497), the human B-cell hybridoma technique (Kosbor et al., (1983) *Immunol Today* 4:72; Cote et al., (1983) *Proc Natl Acad Sci* 80:2026-2030) and the EBV-hybridoma technique (Cole et al., (1985) *Monoclonal Antibodies and Cancer Therapy*, Alan Rickman Liss Inc, pp 77-96).

In addition, techniques developed for the production of "chimeric antibodies", the splicing of mouse antibody genes to human antibody genes to obtain a molecule with appropriate antigen specificity and biological activity may be used (Morrison et al., (1984) *Proc Natl Acad Sci* 81:6851-6855; Neuberger et al., (1984) *Nature* 312:604-608; Takeda et al., (1985) *Nature* 314:452-454).

Alternatively, techniques described for the production of single chain antibodies (U.S. Pat. No. 4,946,779) can be adapted to produce the substance specific single chain antibodies.

Antibody fragments which contain specific binding sites for the substance may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W D et al., (1989) *Science* 256:1275-128 1).

Antibodies may be used to modify the function of PntR through introduction of PntR-specific antibodies in the fungus to mask its function.

Large Scale Application

In one preferred embodiment of the present invention, the methods of the present invention are used for large scale applications. In particular, the methods of the present invention may be used for the large scale production of enzymes such as xylanases for industrial use. The POI of interest can be human antibodies (Ward et al 2004 Appl Envirom Microbiol v 70: 2567-2576), lactoferrin (Ward et al, 1991 Gene, v 122: 219-223), growth hormone, interleukin 6, superoxide dismutase (Davies R. W. in "Molecular industrial Mycology systems and applications for filamentous fungi" (S. A. Leong and R. M. Berka, eds.), pp. 45-58. Morris-Bekker, New York-Basel-Hong Kong, 1991).

Use of PntR Sequences

As recited above, the identification of the transcription repressor PntR in different species enables modified cells to be generated in which PntR expression is knocked down such that expression of genes under the control of an XlnR promoter is increased. Accordingly, the PntR sequences can be used in the identification of suitable means of knocking down expression.

Thus, the present invention further relates to the use of the nucleotide sequences encoding PntR in generating vectors or systems for the knock down or knock out of PntR expression. Suitable vectors are described, for example, in the Examples section herein and include systems for homologous recombination for gene disruption. Preferably, such constructs may introduce a PntR variant lacking the Zn$_2$Cys$_6$ binuclear cluster.

In addition, the present invention relates to the use of such expression vectors or systems in the generation of host cells which have lower than natural levels of PntR expression and further comprise genes encoding a POI under the control of the XlnR promoter. Such host cells are useful in protein production.

Accordingly, the invention further provides a host cell expressing a POI under XlnR regulation to produce a POI for use in the manufacture of a food product.

Food

The compounds may be used as—or in the preparation of—a food. Here, the term "food" is used in a broad sense—and covers food and food products for humans as well as food for animals (i.e. a feed). In a preferred aspect, the food is for human consumption.

The food may be in the form of a solution or as a solid—depending on the use and/or the mode of application and/or the mode of administration.

Food Ingredients and Supplements

The POIs may be used as a food ingredient.

As used herein the term "food ingredient" includes a formulation, which is or can be added to functional foods or foodstuffs and includes formulations which can be used at low levels in a wide variety of products that require, for example, acidifying or emulsifying.

The food ingredient may be in the form of a solution or as a solid—depending on the use and/or the mode of application and/or the mode of administration.

The compounds may be—or may be added to—food supplements.

Functional Foods and Nutraceuticals

The POIs may be—or may be added to—functional foods.

As used herein, the term "functional food" means food which is capable of providing not only a nutritional effect and/or a taste satisfaction, but is also capable of delivering a further beneficial effect to consumer.

Although there is no legal definition of a functional food, most of the parties with an interest in this area agree that they are foods marketed as having specific health effects.

Food Products

The enzymes or POIs produced by the improved method of the present invention can be used in the preparation of food products such as one or more of: confectionery products, dairy products, meat products, poultry products, fish products and bakery products.

For certain aspects, preferably the foodstuff is a bakery product—such as bread, Danish pastry, biscuits or cookies.

The present invention also provides a method of preparing a food or a food ingredient, the method comprising admixing POI produced by the process of the present invention with another food ingredient. The method for preparing or a food ingredient is also another aspect of the present invention.

Paper Industry

Xylanases, including those which are under the control of XlnR, can be used for paper bleaching. In addition, other POIs such as endoglucanase can be used for textile applications.

Pharmaceutical

POIs such as antibodies, for example, can be used in pharmaceuticals. See, for example, Ward et al. 2004.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

EXAMPLES

The invention is now further illustrated in the following non-limiting examples.

1. Fungal strains and growth conditions. The *A. nidulans* strain pyrG89 argB2 was obtained from Prof. C. Scazzocchio (Institut de Genetique et Microbiologie, Orsay, France). The *A. niger* N402 strain (cspA1) was obtained from TNO Nutrition and Food Research Institute (Netherlands). The *A. tubingensis* 1M-7, 4M-147 and 10M-61 strains were from Danisco collection of cultures. Strains were maintained on either minimal on complete medium.

Minimal medium (MM) contained (per 1 l): 1 g of $NaNO_3$, 1.5 g of $KH_2PO_4$, 0.5 g of $KCl$, 0.5 g of $MgSO_4$ and 50 ml of trace elements according to Vishniac and Santer, 1957 (10 g EDTA, 4.4 g $ZnSO_4 \times 7H_2O$, 1 g $MnCl_2 \times 4H_2O$, 0.32 g $CoCl_2 \times 5H_2O$, 0.22 g $(NH_4)_6Mo_7O_{24} \times 4H_2O$, 1.47 g $CaCl_2 \times 2H_2O$, 1 g $FeSO_4 \times 7H_2O$). 1% fructose was used as a carbon source, unless otherwise indicated. For auxotrophic strains, the necessary supplements were added as required: 10 mM of uridine and 2.5 mM of arginine. For complete medium (CM), minimal medium was supplemented with 10 g of fructose, 2 g peptone, 1.5 g casamino acids, 1 g yeast extract and 10 ml of 100× Vitamin Solution (50 mg thiamine HCl, 10 mg biotin, 100 mg nicotinic acid, 200 mg Ca panthothenate, 50 mg pyridoxine HCl, 100 mg riboflavin, 500 mg para-amino-benzoic acid) filter sterilised (Cove, 1966). Before autoclavation, pH of the media was adjusted to 5.5 for *A. tubingensis*, 6.0 for *A. niger*, 6.5 for *A. nidulans*. For a solid medium agar was added to 3%. Liquid cultures were inoculated with 106 spores/ml and incubated on a rotary shaker at 180-220 rpm. *A. nidulans* was cultivated at 37° C., whereas *A. tubingensis* and *A. niger* strains at 32° C. All fermentations were run in flasks.

For DNA preparations, fungal strains were grown overnight on CM and mycelia samples were harvested on a funnel and frozen in liquid nitrogen.

2. Cloning of the *A. nidulans* pntR gene and construction of the deletion vector pPntRΔ-pyrG. The region containing a putative XlnR homologue from the *A. nidulans* contig 1.7 see the *Aspergillus* database at the Broad Institute website for contig position 23984 to 26497 bp) was amplified by PCR from the *A. nidulans* genomic DNA. To extract DNA from mycelia samples, 0.2 g of biomass frozen in liquid nitrogen were ground to powder and resuspended in 0.8 ml of the extraction buffer: 0.2 M Tris-HCl, pH 8.0, 1% SDS, 1 mM EDTA. After 10-20 min of incubation on ice, DNA was isolated by a standard phenol-chloroform extraction method and, after precipitation with ethanol, was resuspended in 100-200 μl $H_2O$ followed by treatment with 50 μg of RNAse A (Qiagen) for 15 min at 37° C. About 50-100 ng of the genomic DNA was further used for PCR amplifications. All PCR reactions were run with an Expand High Fidelity PCR Amplification System (Roche) in a total volume of 50 μl. The reaction contained 5 μl of 10× Expand buffer, 3.5 units of a Taq and Pfu DNA polymerase mixture, 200 μM dNTP mixture, 50 ng of a DNA template and 40 pmol of each primer of the following sequence:

```
R1.7 T40    5' GCGGGGAGCATAATATATACAGGTCCAGTT 3'
and

R1.7 B3795  5' TGAATCTCGTCTTGGGAAGGATTCAAGATG 3'.
```

Amplification was performed using the following program: 94° C. for 3 min, 30 cycles of 94° C. for 45 sec, 56° C. for 1 min and 72° C. for 3 min. An additional extension cycle of 10 min at 72° C. was applied. The PCR product of 3.75 kb was purified on a gel and cloned into the pCR-Blunt II vector (Invitrogen) resulting in plasmid pSFH1 (FIG. 1). This fragment covers the putative ORF with 5' and 3' flanking regions of 0.75 and 0.5 kb, respectively (see SEQ ID NO: 1). The coding region can be translated as a single ORF without any stop codons. However, in the *A. nidulans* Database this sequence is annotated to contain one intron, which does not interrupt the ORF. This putative intron might be predicted by computer analysis, since no experimental data on the pntR cDNA has been available previously.

FIG. 1. A map of plasmid pSFH1.

The M13 forward (5' GTAAAACGGCCAG 3' (SEQ ID NO: 10)) and reverse (5' CAGGAAACAGCTATGAC 3' (SEQ ID NO: 11)) primers were used to check the authenticity of the sequence and the orientation of the insert cloned. DNA sequencing was performed on an ABI 3100 Sequence Analyser (Applied Biosystems) using a BigDye Terminator v3.1 Cycle Sequencing Kit (Applied Biosystems) and 500 ng of a template with 3.2 pmol of primers.

At the second step, an upstream genomic fragment of 3.4 kb partially overlapping the pntR sequence was amplified by PCR under similar conditions using a combination of the primers present below:

```
R1.7 T Spe 603
5' GGACTAGTGCAGGATGATCGCATCGACAATTATATAAG 3'
(SEQ ID NO: 12)

R1.7 B Nde 4008
5' AAAGTCTGGAAGGAATCAGGGAAAAGCAAG 3'
(SEQ ID NO: 13).
```

The purified PCR product was cut with the restriction enzymes SpeI and NdeI. Note that the SpeI site was introduced during the amplification. 2-3 µg of the pSFH1 plasmid mentioned above was digested with the same enzymes, the vector was eluted from an agarose gel using a Gel Extraction Kit (Qiagen) and ligated with the PCR product using a Rapid Ligation Kit (Roche). The ligation mixture was used to transform E. coli TOP10 competent cells (Invitrogen). Transformants were selected on LB plates with 50 µg/ml of kanamycin. 2 µg of the resultant vector was cut with the restriction enzymes NdeI and BstZ17I and filled-in with Klenow fragment of the DNA polymerase I to generate blunt ends. It was then used to insert the 1.9 kb fragment comprising the A. fumigatus pyrG gene, which was isolated from the pCDA21 plasmid (Chaveroche et al., 2000) by the EcoRV cut. The orientation of the insert was checked by the EcoRI and KpnI digestions. A schematic representation of the pPntRΔ-pyrG plasmid used to delete the endogenous copy of the pntR gene in the A. nidulans genome is present in FIG. 2. In the deletion construct the pyrG gene replaces 214 bp of the 5' flanking sequence upstream the ATG codon and 301 bp of the coding part including the $Zn_2Cys_6$ binuclear cluster, thereby rendering the rest of the sequence, if any expressed, inactive.

Figure 2:
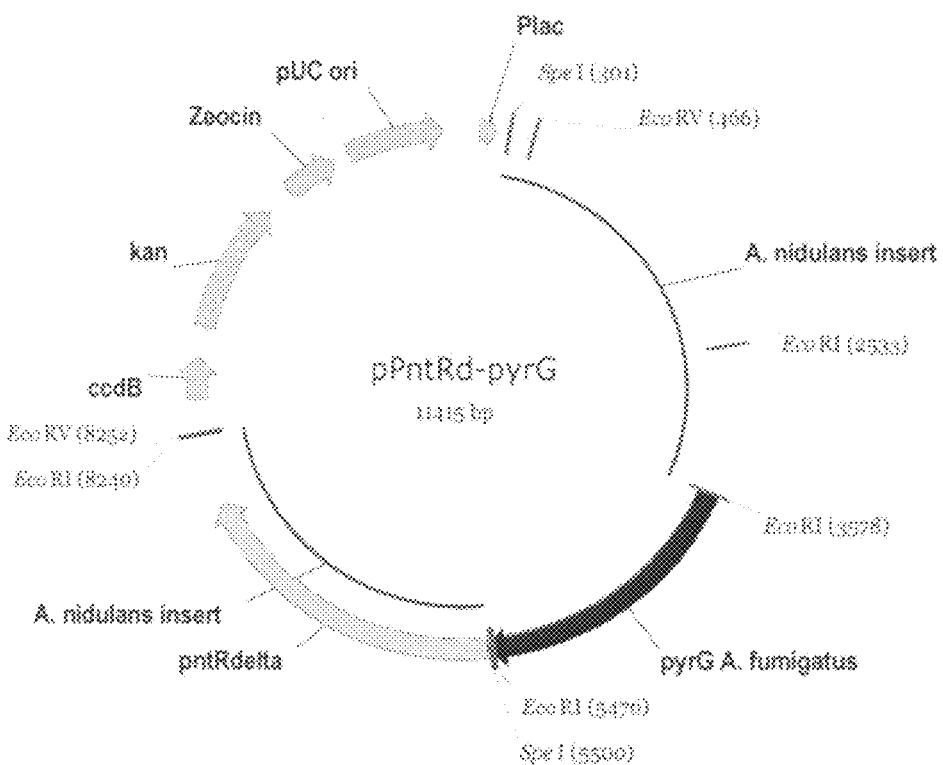
FIG. 2. A map of plasmid pPntRΔ-pyrG.

FIG. 2 shows a map of plasmid pPntRΔ-pyrG.

3. A pntR knockout in A. nidulans. To delete the endogenous pntR gene, the A. nidulans recipient strain pyrG89argB2 was transformed to uridine prototrophy with a linear fragment of 7.7 kb long isolated after digestion of 10 µg of the pPntRΔ-pyrG plasmid with the restriction enzyme EcoRV. Around 1-3 µg of the fragment purified from an agarose gel with a Gel Extraction Kit (Qiagen) was taken into transformation. A standard method of fungal transformation was applied (Tilburn et al, 1983). Briefly, the recipient strain was grown overnight in 400 ml of MM with 1% glucose and supplements at 25° C. Mycelium was harvested, washed with water and 1 g was resuspended in 10 ml of 1.2 M $MgSO_4$ solution buffered with 10 mM Na-phosphate, pH 5.8. Mycelium was treated with 40-50 mg/ml of non-purified Glucanex (Laffort, France) at 30° C. with a gentle agitation. After 2-3 h of incubation, when a sufficient number of protoplasts could be monitored after a microscopic examination, the digested mycelium was diluted with the same buffer and protoplasts were separated during centrifugation with an overlay of 0.6 M D-sorbitol buffered with 100 mM Tris, pH 7.5.

Figure 3:
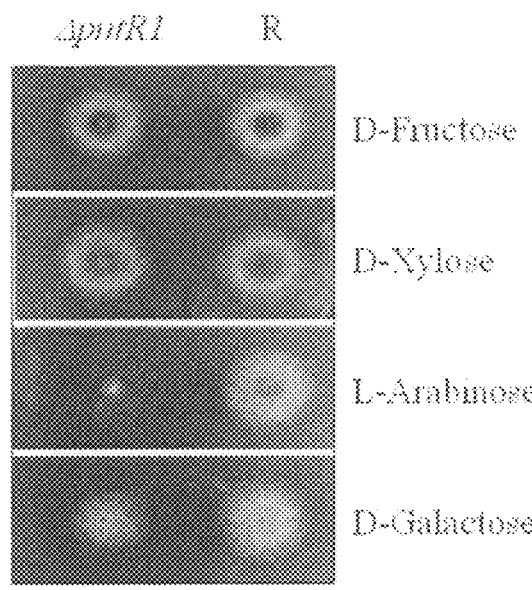
FIG. 3. Growth test of one of the typical *A. nidulans* ΔpntR deletants (ΔpntR1) in comparison to the recipient pyrG89 argB2 strain (R) on MM with 1% of each carbon source as indicated.

Protoplasts collected from the interface were washed twice with 1.2 M sorbitol solution containing 10 mM Tris, pH 7.5 and 10 mM $CaCl_2$ (STC) and resuspended in STC at concentration $10^7$-$10^8$/ml. 200 µl of the protoplast solution was incubated for 20 min on ice with 1-3 µg of the DNA fragment and 50 µl of 60% PEG 6000 solution containing 10 mM Tris, pH 7.5 and 10 mM $CaCl_2$. After adding extra 0.5 ml of the same PEG solution, the mixture was left at room T for 5 min and plated on MM with 1M sucrose and arginine as a supplement. Transformants were selected for uridine prototrophy. After 3 days of incubation at 37° C. around 100-150 transformants were obtained and analysed. Initial screening for a pntR deletant was performed on MM test plates with 1% of each carbon source, as indicated (FIG. 3). Out of 62 candidates tested, 10 had severely impaired growth on L-arabinose and slightly delayed growth on D-galactose (FIG. 3). They were further tested for improvement of β-xylosidase activity on MM containing 0.1% fructose with 10 mM L-arabinose and 10 µg/ml of 4-methyl-umbelliferyl-β-D-xyloside as a substrate. All exhibited strong fluorescence at 254 nm, whereas the recipient strain did not.

FIG. 3 shows the results of a growth test of one of the typical A. nidulans ΔpntR deletants (ΔpntR1) in comparison to the recipient pyrG89 argB2 strain (R) on MM with 1% of each carbon source as indicated.

Figure 4:
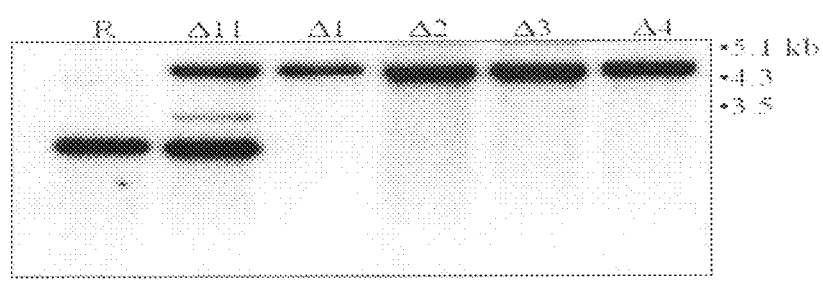
FIG. 4. Southern blot analysis of the genomic DNAs from *A. nidulans* ΔpntR transformants digested with the ClaI restriction enzyme. Blots were probed with the 5' fragment of pntR and washed with 1×SSC, 0.1% SDS at 60° C.

To check, if the native pntR locus was disrupted, a few transformants were analysed by Southern blot analysis (Sambrook et al, 1989). 5-10 µg of the genomic DNA isolated from different transformants as described previously was cut with 50 U of the restriction enzyme ClaI (Biolabs) for 3 h and separated on a 0.7% agarose gel in the TBE buffer. Digested samples were transferred on a Nylon membrane (Amersham) and hybridized with $P^{32}$-radioactively labeled DNA fragment of the pntR gene. This fragment was isolated by cutting the pSFH1 plasmid with EcoRI and eluting the fragment of 0.94 kb long. 50 ng of the fragment was labeled with 50 µCi of $P^{32}$-dCTP using a Random Priming Kit (Stratagen). As seen in FIG. 4, transformants ΔpntR1, ΔpntR2, ΔpntR3, ΔpntR4 contained only one band of the pntR gene of a different size, whereas ΔpntR11 contained, in addition, the wild type copy. The size of the upper band corresponds to the one expected after the insertion of the pyrG gene. The knockout strain ΔpntR1 was chosen for further studies.

FIG. 4 shows Southern blot analysis of the genomic DNAs from A. nidulans ΔpntR transformants digested with the ClaI restriction enzyme. Blots were probed with the 5' fragment of pntR and washed with 1×SSC, 0.1% SDS at 60° C.

4. Effect of the pntR deletion on the expression level of extracellular carbohydrolases produced by A. nidulans. To test whether the putative XlnR homologue, PntR, affects xylanase and α-L-arabinofuranosidase expression in A. nidulans, the ΔpntR1 deletant was checked for the corresponding activities upon induction by D-xylose or L-arabitol. With this purpose, A. nidulans cultures were first pregrown for 16 h on CM, washed with $H_2O$ and 1 g of wet mycelium was transferred in 100 ml of MM containing 0.1% fructose together with the inducing sugar (D-xylose or L-arabinose) or polyol (L-arabitol) at 10 mM of the final concentration, as indicated. Cultures without the inducer were used to monitor the basal level of expression. Extracellular activities were measured 9 and 24 h after the transfer. Xylanase and β-Glucanase activities were measured at 40° C., whereas α-arabinofuranosidase and β-galactosidase at 30° C. In all assays, an aliquot of culture samples (20-200 µl) was added to 30 mM Na-acetate buffer, pH 5.0 together with a substrate to give 1 ml of a final volume. One tablet of Xylazyme T-XYZ1000 (Megazyme), one tablet of Beta-Glucazyme (Megazyme), 0.2 mg of p-nitrophenyl-α-L-arabinofuranoside and 1 mg of o-nitrophenyl-β-D-galactoside (Sigma) were used as substrates for xylanase, β-glucanase, α-L-arabinofuranosidase and β-galactosidase, respectively. Enzymatic reactions were incubated for various time periods and stopped by adding either 9 ml of 0.2 M Tris-Base (for xylanase and β-glucanase) or 0.5 ml of 1 M Na$_2$CO$_3$ (for α-L-arabinofuranosidase and β-galactosidase). Optical density of the reaction mixtures was measured at 590, 405 or 420 nm, respectively. Activities were expressed in relative O.D. units, unless stated otherwise.

Figure 5:
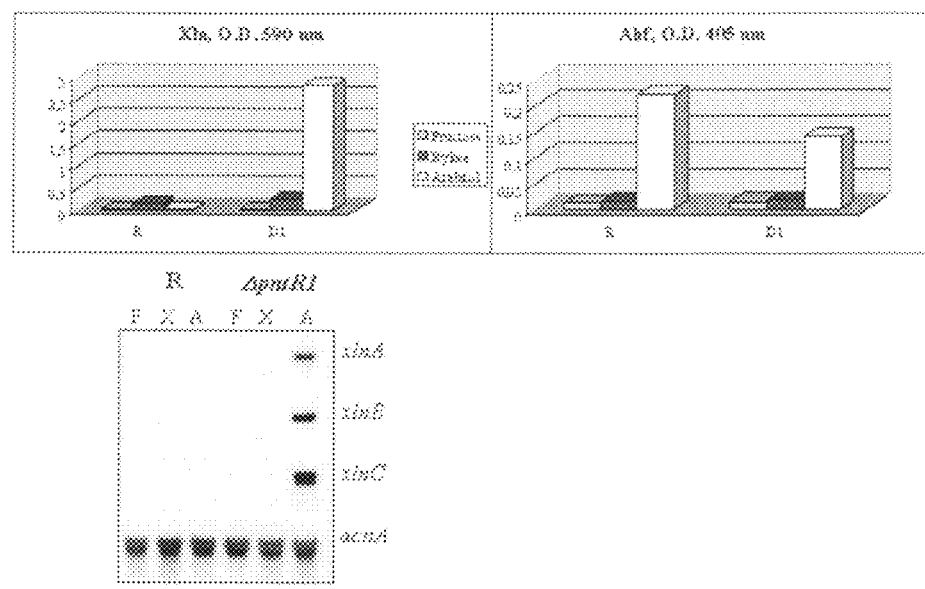
FIG. 5. Enzyme assays (top) and transcriptional analysis (bottom) of the recipient (R) and ΔpntR1 deletant (D1) strains after induction by 10 mM of D-xylose or L-arabitol.

As seen in FIG. 5, the absolute xylanase activity was 20-fold higher in the ΔpntR1 deletant upon the induction by L-arabitol than in the recipient strain on D-xylose. In the latter strain xylanase level was negligible on L-arabitol. A similar, but less pronounced effect was observed on L-arabinose (not shown but done). In parallel, overexpression of xylanase was followed by a slight decrease of α-arabinofuranosidase activity. One can speculate that phenomenon observed can be explained by changes in metabolism of L-arabinose (presumably, resulting in elevated intracellular concentrations of intermediate metabolite, L-arabitol, or thereof). This leads to higher activation capacities of XlnR and, as a consequence, more efficient transcriptional activation of the genes under its control, such as xylanases, as assessed by Northern blot analysis. PntR apparently positively affects α-arabinofuranosidases as well as the enzymes responsible for L-arabinose metabolism.

FIG. 5 shows enzyme assays (top) and transcriptional analysis (bottom) of the recipient (R) and ΔpntR1 deletant (D1) strains after induction by 10 mM of D-xylose or L-arabitol. Samples for xylanase assays and RNA isolation were taken 9 h after the transfer, whereas α-arabinofuranosidase measurements were performed 24 h after the transfer. For xylanase assay, 100 μl of culture liquid was used in reaction, which was incubated for 10 min. For α-arabinofuranosidase, 200 μl were added to give a final volume of 1 ml and the reaction was incubated for 60 min. Approximately 10 μg of the total RNA was loaded per lane on a Northern blot and hybridized with three xylanase-derived probes. The acnA (γ-actin) probe was used as an internal control to normalize the amount of RNA loaded. Total RNAs were isolated from mycelia samples using RNeasy Plant Mini Kit (Qiagen) in accordance to recommendations of the supplier, denatured with glyoxal and separated on 1% agarose gel as described by Sambrook et al (1989). Xylanase probes were amplified by PCR from the genomic DNA, as described previously, using gene specific primers:

```
XlnA T675      5' AATCTCTCCTAGTTCTCTGTTGCGCTGC 3'
               (SEQ ID NO: 14)
and XlnA B1380     5' TACTCTGGTACCCCTCCGTTGCAACAAT 3';
               (SEQ ID NO: 15)

XlnB T651      5' ATGGTCTCCTTCTCATCCCTTCTCCT 3'
               (SEQ ID NO: 16)
and XlnB B1354     5' CGGTAATAGAAGCAGATCCACTGCTC 3';
               (SEQ ID NO: 17)

XlnC T1053     5' TGATCTTTTTGTCGCGGCCGGCAAAT 3'
               (SEQ ID NO: 18)
and XlnC B1876     5' TGGCGTAGCTCGCAGAGTCCAGGCTAAT 3'
               (SEQ ID NO: 19).
```

The acnA probe was prepared from the 2.5 kb BamHI-KpnI fragment of the pSF5 plasmid (Fidel et al., 1988). Blots were washed with 1×SSC, 0.1% SDS at 55° C.

In addition, we measured the activities of intracellular L-arabinose and D-xylose reductases, as well as L-arabitol and D-xylitol dehydrogenases, and monitored their transcription.

5. Cloning of the pntR homologue from A. niger. The pntR homologous sequence was cloned by PCR amplification of the A. niger 402 genomic DNA using primers designed after alignment of the structural parts of the pntR gene from A. nidulans and the equivalent sequence from the A. fumigatus Database. The following primers were applied:

```
PntR1.7 T104
5' GTGACTCTTGTCATGCTCGCCGCGTTCGATGCGAC 3'
(SEQ ID NO: 20)
and

PntR1.7 B6593
5' AGAGCCAACCCGGTTCCCTTCCTTGTCCAC 3'
(SEQ ID NO: 21).
```

The PCR conditions were the same as described before, except for 54° C. for the annealing temperature and 2 min for the amplification time. The PCR product obtained was cloned into the pCR 4 TOPO vector according to instructions of the supplier (Invitrogen). Competent E. coli TOP10 cells (Invitrogen) used for transformation were plated on LB plates with 100 mg/ml of ampicillin for selection of the appropriate construct. The final plasmid pPntR-AN14 was used as a template to sequence the genomic insert. The partial sequence of the putative A. niger pntR gene of 2.3 kb was established from the reverse and forward primers as well as from the gene specific primers:

```
PntR 1201      5' TGGAGTCGAGCTTGCCTCGAAAGC 3'
               (SEQ ID NO: 22)
and PntR B1500     5' CAGGAAGAAGCCGAAGATAGAG 3'
               (SEQ ID NO: 23).
```

Figure 6:
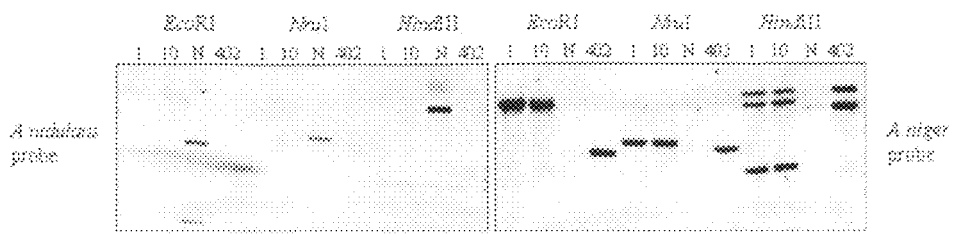
FIG. 6. Southern blots of the genomic DNAs from *A. nidulans* (N), *A. niger* (402) and *A. tubingensis* (1 and 10) strains.

The sequence is presented in the SEQ ID NO: 3. Note that parts coding for the N-terminal DNA binding domain and COOH-terminus are lacked. In contrast to A. nidulans, the ORF of the pntR homologue from A. niger is interrupted by one putative intron from position 1063 to 1115 bp, whose position was predicted by virtue of the conservative sequences found at its 5' and 3' borders. Though sequence alignment showed 69% of identity between the two genes, they did not give an obvious signal on Southern blots upon cross-hybridization (FIG. 6). However, the A. tubingensis genome contains a pntR-related sequence very similar to that from A. niger.

FIG. 6 shows Southern blots of the genomic DNAs from A. nidulans (N), A. niger (402) and A. tubingensis (1 and 10) strains. 5-10 μg of DNAs were digested to completion with different restriction enzymes, as indicated, separated on a 0.7% agarose gel, transferred on a Nylon membrane (Amersham) and hybridised either with the A. nidulans or A. niger pntR probe. The 3 kb long SpeI-PstI fragment from plasmid pSFH1 served as an A. nidulans probe, while the 2.3 kb EcoRI fragment from plasmid pPntR-AN14 was used as an A. niger probe. Both probes cover mostly the structural part of the corresponding pntR genes. Blots were washed with 2×SSC and 0.1% SDS at 55° C.

6. Cloning of the pntR gene from *A. tubingensis*. The pntR homologous sequence from *A. tubingensis* 4M-147 strain was cloned from the corresponding genomic library. To make such a library, the *A. niger* 4M-147 genomic DNA was isolated as described earlier, and 10 µg of DNA was partially digested with Tsp509T (New England BioLabs). Fragments of a size between ca. 5 and 10 kb were purified from a 0.7% agarose gel using a Gel Extraction Kit (Qiagen). 100 ng of fragments were ligated into 1 µg of the EcoRI-digested and dephosphorylated ZAP TI vector (Stratagene) in a total volume of 5 µl using 2 Weiss units of T4 DNA ligase (Roche). 2 µl of the ligation mixture was packaged into Gigapack II packaging extract (Stratagene) following recommendations of the supplier. In total, around $6.5 \times 10^5$ independent pfu were obtained in a primary library using the *E. coli* XL1-Blue strain as a host. $2.5 \times 10^5$ pfu were amplified as indicated in the manual (Stratagene) to give a titer of $3 \times 10^8$ pfu/ml with approximately 6% without inserts.

Out of $3-5 \times 10^4$ pfu tested in a primary screen, 20-25 gave a positive signal upon filter hybridization with the $P^{32}$-labeled 2.3 kb EcoRI fragment of the pPntR-AN14 plasmid, which contains the *A. niger* pntR gene. Five of them were purified to individual plaques and the corresponding phagemid DNAs were isolated using a Rapid Excision Kit (Stratagene). Sequence of the inserts was established using the reverse and forward primers as well as the pntR gene-specific primer:

```
PntR1.7 B178: 5' AGAGCCATTTGGAACTGGGCCAGACCCTGC 3'
               (SEQ ID NO: 24).
```

Finally, one of the clones, pPntR-AT12, carrying the entire *A. tubingenis* pntR gene with the longest 5' and 3' flanking regions was partially sequenced using the following oligonucleotides:

```
PntR At T1:    5' GGCTAAGGACCGGTTCTTTCGC 3';
               (SEQ ID NO: 25)

PntR At B1:    5' GCCGATGGCCTGCGGATGCG 3';
               (SEQ ID NO: 26)
```

The sequence of oligos PntR 1201 and PntR B1500 was shown in the previous section.

In total, a sequence of 3914 bp was determined, which includes the entire structural part of the pntR gene flanked by upstream 485 bp and downstream 878 bp (see SEQ ID NO: 5). Similar to *A. niger*, the coding region of the pntR gene from *A. tubingensis* is interrupted by one intron, whose relative position is conserved within the gene. To check, if the pntR deletion in *A. tubingensis* has a similar beneficial effect on xylanase production as in *A. nidulans*, the corresponding gene was disrupted.

7. Disruption of the pntR gene in *A. tubingensis* 1M-7 strain. In contrast to *A. nidulans*, where a part of pntR was deleted, the endogenous copy of the pntR gene in *A. tubingenis* was interrupted by the insertion of the hph gene from *E. coli* conferring the fungal cell resistance to hygromycin B. A disruption construct was made by cloning a part of the *A. tubingensis* pntR coding region, which lacks both the N- and C-termini, into plasmid pAN7-1. This vector harbors the hygromycin B resistance gene under the control of the gpdA promoter (Punt and van den Hondel, 1992). In this case, homologous recombination within the pntR fragment will result in two disrupted copies of pntR. One will be truncated at the 3' end, another at the 5' end.

With this purpose, the pntR fragment from 631 bp to 2803 bp was amplified by PCR with the help of primers:

```
PntR T631
5' ATCGAGCCTTTCCCAGATCTCGCTGCCTTCGCAG 3'
(SEQ ID NO: 27)
and

PntR BSal
5' CGCTTGTCGACGCAGCCGCTCTACAATCAGCAAGAGAAG 3'
(SEQ ID NO: 28).
```

The PCR reaction was run with 20 ng of plasmid pPntR-AT12 as a template and at 56° C. as the annealing temperature for 2 min of the extension time. The purified PCR product (0.5 µg) was digested with the restriction enzymes SalI and BglII (10 units of each), whose restriction sites were introduced at the both termini during amplification. It was then cloned into the pAN7-1 vector cut by XhoI and BglII. These digestions eliminated a part of the gpdA promoter, which remains, however, functional. 0.2 µg of the eluted vector and 0.3 µg of the insert were ligated with 3 Weiss units of T4 DNA ligase in a total volume of 20 µl containing 10 µl of the 2× ligation buffer (Roche). Ligation reaction was transformed into *E. coli* TOP10 competent cells (Invitrogen) plated on LB plates with 100 µg/ml of amplicillin. A schematic representation of the disruption construct pAN7-ΔPntR is present below (FIG. 7).

Figure 7:
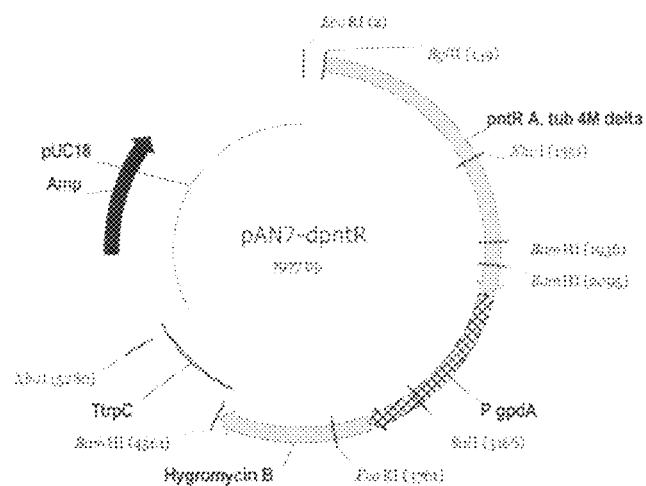
FIG. 7. A map of plasmid pAN7-ΔPntR.

FIG. 7 shows a map of plasmid pAN7-ΔPntR.

Figure 8:
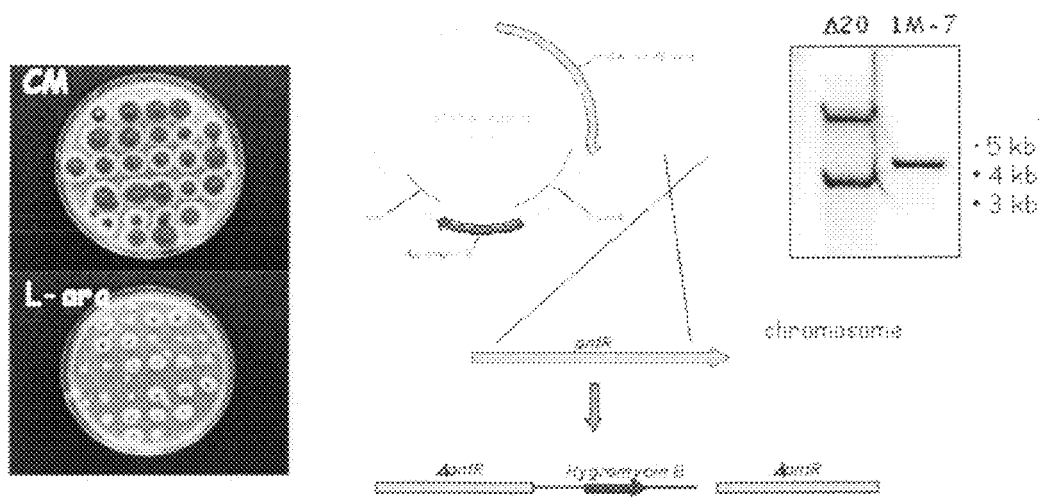
FIG. 8. Growth test of *A. tubingensis* 1M-7 transformed with plasmid pAN7-ΔPntR on CM and MM with 1% of L-arabinose (at left) and a Southern blot of the deletant Δ20 and 1M-7 strains (at right).

This plasmid was used to transform *A. tubingensis* 1M-7 strain. Transformation conditions were similar to those used for *A. nidulans* with minor modifications, as indicated below. 1M-7 strains was grown overnight on CM and after treatment the mycelium with 50 mg/ml of Glucanex (Laffort), protoplasts harvested were transformed with 5-10 µg of plasmid pAN7-ΔPntR. Transformants were selected on MM with 1M of sucrose and 100 µg/ml of hygromycin B. In total, 300-400 resistant colonies were obtained, and among 70 transformants analysed 25 were positive, as judged by a plate growth test on 1% L-arabinose (FIG. 8). Non-growing transformants (15 tested) also showed a strong fluorescence on MM plates containing 0.1% fructose with 10 mM L-arabinose and 10 µg/ml of 4-methyl-umbelliferyl-β-D-xyloside indicating up-regulation of β-xylosidase. Several transformants were analysed by Southern blot analysis for disruption of the native pntR locus in *A. tubingensis* 1M-7 genome. A typical pattern of hybridisation is shown in FIG. 8. 5 µg of DNAs from the recipient and transformants Δ2 and Δ20 were cut to completion with 50 units of NcoI and probed with the $P^{32}$-labeled PCR fragment of the pntR gene from 631 bp to 2803 bp. As expected, two bands resulted from integration of the pAN7-ΔPntR plasmid in the *A. tubingensis* pntR locus were observed on Southern blot in contrast to a single band from the recipient sample.

FIG. 8 shows the results of a growth test of *A. tubingensis* 1M-7 transformed with plasmid pAN7-ΔPntR on CM and MM with 1% of L-arabinose (at left) and a Southern blot of the deletant Δ20 and 1M-7 strains (at right). DNAs were digested with NcoI and probed with the pntR fragment as indicated. A scheme of homologous integration of the disruption plasmid pAN7-ΔPntR is shown.

8. Improved xylanase and β-glucanase production in *A. tubingensis* ΔpntR deletant strains. To check the effect of the pntR disruption on protein production, *A. tubingensis* was cultivated under different growth conditions and enzymatic activities of a number of extracellular proteins were measured in culture liquids. In the first set of experiments, *A. tubingensis* strains were cultivated for 40 h on MM with 1% fructose and 0.1% yeast extract with or without of 10 mM L-arabinose.

In parallel, they were grown or 1% xylose and 0.1% yeast extract. Purely fructose containing medium was considered as a neutral, non-induced conditions, whereas L-arabinose or D-xylose induced extracellular activities. The biomass accumulated during growth was nearly equal for all strains. Activities were measured as in the case of *A. nidulans*, except for xylanase, which was assayed in 0.2 M Na-phosphate-0.1 M citric acid buffer, pH 3.5.

Figure 9:
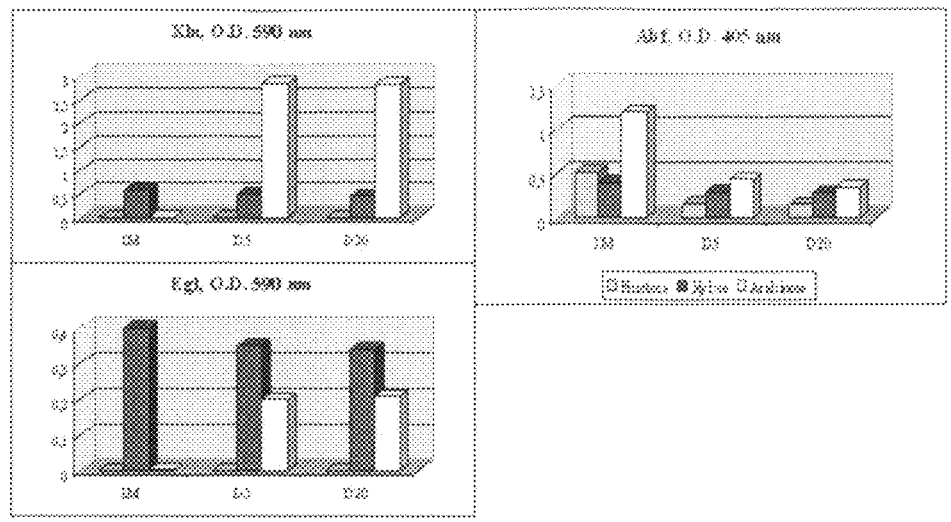
FIG. 9. Activities of xylanase (Xln), β-glucanase (Egl) and α-arabinofuranosidase (Abf) after growth of *A. tubingensis* 1M-7 recipient and pntR deleltant D5 and D20 strains on 1% fructose+0.1% YE, 1% fructose+0.1% YE+10 mM L-arabinose and 1% xylose+0.1% YE. 20 μl of culture samples were used for both xylanase and β-glucanase measurements, whereas 100 μl were used for α-arabinofuranosidase. Reactions were run for 10 min for xylanase and β-glucanase and for 60 min for α-arabinofuranosidase. Activities are expressed in O.D.

As seen in FIG. 9, both xylanase and β-glucanase activities were increased on L-arabinose containing medium. In fact, the absolute value of xylanase activity was 5-fold higher in comparison to xylose induction conditions. In parallel, α-arabinofuranosidase activity decreased nearly 3 times. Taken together, these results show that knocking out the pntR gene in both *A. tubingensis* and *A. nidulans* results in exactly identical phenotypes and improved expression levels of xylanases and other XlnR-regulated genes, like β-xylosidase and β-glucanase, under L-arabinose induction conditions. In addition, activities of L-arabinan degrading complex are less pronounced which can be beneficial for xylanase preparations used in industrial applications.

FIG. 9 shows the activities of xylanase (Xln), β-glucanase (Egl) and α-arabinofuranosidase (Abf) after growth of *A. tubingensis* 1M-7 recipient and pntR deletant D5 and D2O strains on 1% fructose+0.1% YE, 1% fructose+0.1% YE+10 mM L-arabinose and 1% xylose+0.1% YE. 20 µl of culture samples were used for both xylanase and β-glucanase measurements, whereas 100 µl were used for α-arabinofuranosidase. Reactions were run for 10 min for xylanase and β-glucanase and for 60 min for α-arabinofuranosidase. Activities are expressed in O.D.

Figure 10:
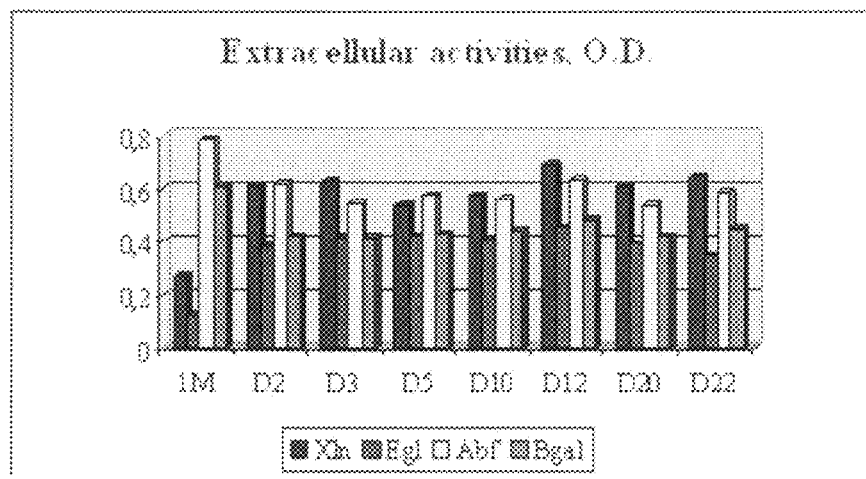
FIG. 10. Activities of xylanase (Xln), β-glucanase (Egl), α-arabinofuranosidase (Abf) and β-galactosidase (Bgal) after growth of *A. tubingensis* 1M-7 recipient and pntR deleltant strains D2, D3, D5, D10, D12, D20, D22 on the complex medium with sugar beet pulp.

In another experiment, *A. tubingensis* strains were fermented for 4-6 days on an industrially used complex medium with 3% sugar beet pulp, 3% wheat bran and 0.17% $(NH_4)_2SO_4$, pH 3.5. Following the fermentation, activities were measured in culture fluid samples (FIG. 10). Again, xylanase and β-glucanase activities were 2-3 times increased, while α-arabinofuranosidase and β-galactosidase was slightly decreased. These conditions are relevant for industrial production of xylanase or heterologous proteins from the xylanase or any other strong XlnR-regulated promoter on cheap media.

FIG. 10 shows the activities of xylanase (Xln), β-glucanase (Egl), α-arabinofuranosidase (Abf) and β-galactosidase (Bgal) after growth of *A. tubingensis* 1M-7 recipient and pntR deletant strains D2, D3, D5, D10, D12, D20, D22 on the complex medium with sugar beet pulp. 0.5 µl of culture samples were used for both xylanase and β-glucanase measurements, whereas 25 µl were used for α-arabinofuranosidase and β-galactosidase. Reactions were run for 10 min for all the enzymatic assays. Activities are expressed in O.D.

9. The Effect of a Deletion of the Gene Encoding the PntR Transcription Factor on Metabolism and XlnR-Regulated Gene Expression.

Figure 11:
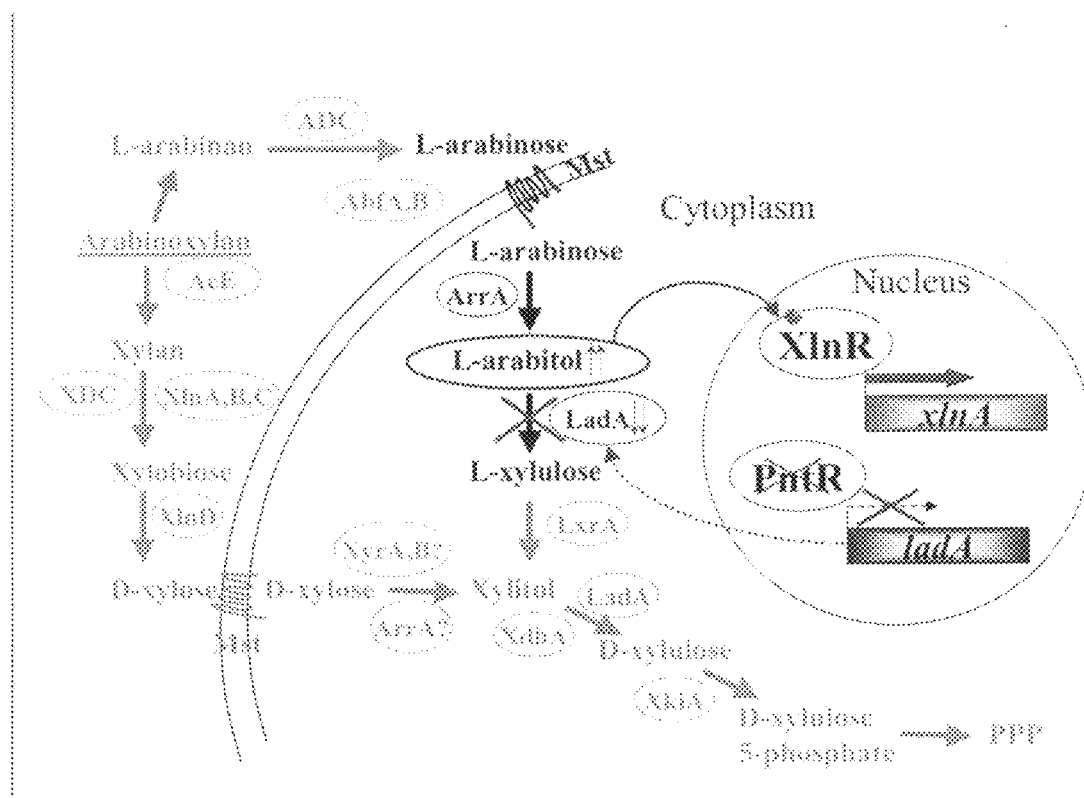
FIG. 11. A scheme of the pathway of arabinoxylan in filamentous fungi and the effect of a deletion of the gene encoding the PntR transcription factor on metabolism and XlnR-regulated gene expression.
Figure 13:
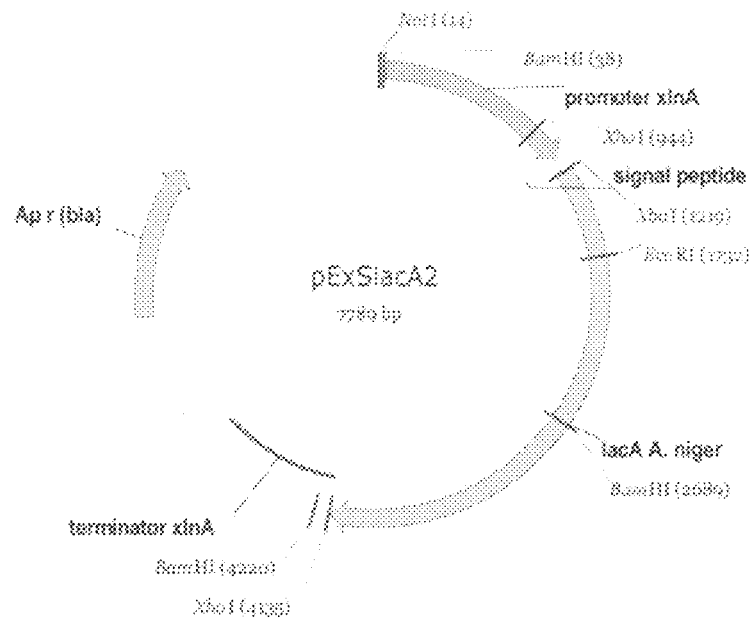
FIG. 13. A map of plasmid pExSlac2.

FIG. 11 shows a schematic of the pathway of arabinoxylan in filamentous fungi and the effect of a deletion of the gene encoding the PntR transcription factor on metabolism and XlnR-regulated gene expression.

AcE denotes all accessory enzymes necessary to hydrolyse various side chain groups on arabinoxylan. XDC and ADC denote xylan and L-arabinan degrading complexes of extracellular enzymes produced by the filamentous fungi. Among them, xylanases (xlnA, xlnB and xlnC) and L-arabinofuranosidases (abfA and abfB) are specified. XlnD codes for beta-D-xylosidase and Mst denotes a monosaccharide transporter. The xylose reduction step is likely to be exerted by more than the one known reductase, XyrA. Either a second putative xylose-induced reductase, XyrB or a yet unknown arabinose reductase (ArrA) could be involved. Xylitol can be converted, at least in *T. reesei*, by both xylitol dehydrogenase (XdhA) and L-arabitol dehydrogenase (LadA). However, L-arabitol is oxidised exclusively by LadA.

Disruption of pntR (shown by crosses) leads to a basal level of transcription of its target genes, including ladA, resulting in a decrease of the LadA enzymatic activity (shown by the downwards arrows), thereby ceasing the downstream metabolic flow. This results in the elevated pool of intracellular L-arabitol, which directly or indirectly activates XlnR mediating the transcription of xlnA and other genes.

10. Analysis of a Primary Structure of the pntR Gene and its Deduced aa Sequence from Different *Aspergilli*.

Figure 12A:
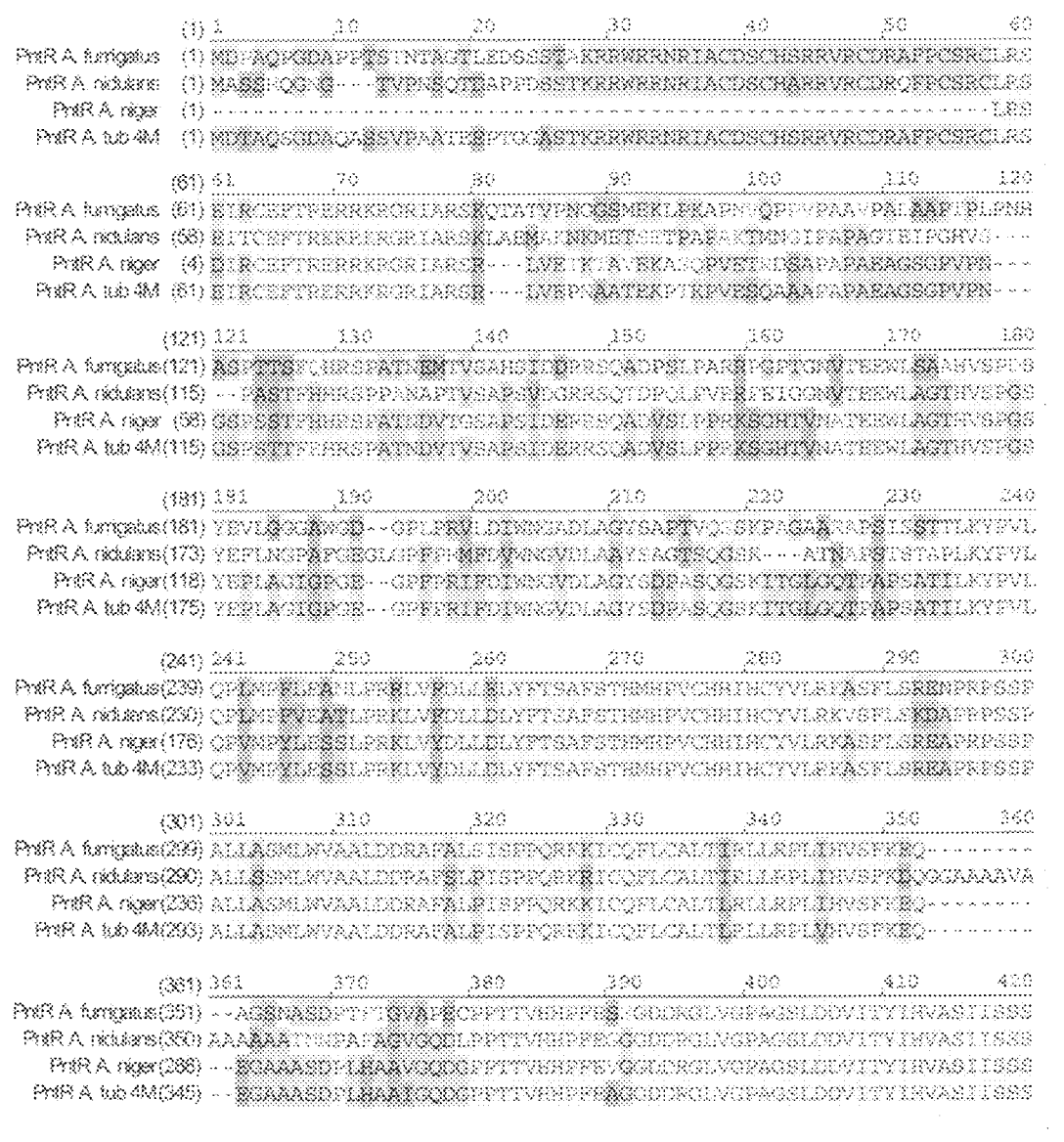

Analysis of the fungal Databases available so far showed that pntR is found primarily in *Aspergillus* species. Nucleotide comparison of the pntR coding regions from four *Aspergillus* species showed 58% of identity. Except for *A. nidulans*, the pntR from the other species contain one intron. At the protein level, the homology is even higher (70%) (see FIG. 12). The alignment showed that the proteins from *A. nidulans* and *A. fumigatus* are evolutionary closer to each other than to *A. niger* and *A. tubingensis*. The homology within the DNA binding domain and especially at the C-terminal part is nearly 100%. The DNA binding domain determines the specificity of this transcription factor. Based on comparison with the DNA binding motif of XlnR, it can be predicted that PntR recognizes other DNA targets. The function of the conservative C-terminal region is not known but this part is the most similar to XlnR. It could be speculated that it is involved in a similar function, as for example, interaction with the inducer or intramolecular interactions in response to the presence of the inducer, since both factors turn out to be activated by L-arabitol. Another conservative region typical for fungal regulators of a $Zn_2Cys_6$ protein family encompassing the stretch EEHREERRRTWW (SEQ ID NO: 29) was mapped from position 492 to 503 aa. All DNA and protein analyses and comparisons were performed using the Vector NTI 9 program package.

12. Heterologous expression of secreted b-galactosidase LacA under the control of the *A. tubingensis* xlnA promoter in *A. nidulans*.

To demonstrate, if a deletion of pntR provides an appropriate background for elevated expression of heterologous proteins, we used the *A. niger* lacA gene coding for a secreted b-galactosidase as a reporter marker. With this purpose an expression vector, where the lacA expression was controlled by the *A. tubingensis* 1 M-7 xlnA promoter and terminator regions, was constructed. For efficient secretion, the xlnA signal sequence was fused in frame with the lacA coding region. Namely, the 3 kb lacA gene was amplified by PCR from the *A. niger* 402 genomic DNA using the corresponding primers:

```
LacA T131
5' CTAGTCTAGAGCCCTGTTGCAGAAATACGTCACTTGGGATG 3';
(SEQ ID NO: 30)

LacA B3031
5' TCCGCTCGAGCTAGTATGCACCCTTCCGCTTCTTGTACTT 3'
(SEQ ID NO: 31).
```

10-15 mkg of pExSlac2 was co-transformed with 0.5-2 mkg of pILJ16 (Johnstone et al., 1985) carrying the *A. nidulans* argB gene into the control *A. nidulans* strain (pyrG89 argB2 pPyrG) and the deletant ΔpntR1 strain (pyrG89 argB2 pntRΔ::pyrG). Transformation was performed as described in Example 3, but transformants were selected on MM plates for arginine prototrophy. Randomly picked transformants were screened for b-galactosidase activity on MM plates with 20 mM D-xylose and 0.005% Xgal. Those, which formed intensive color, were further tested in liquid cultures. *A. nidulans* transformants which integrated the pExSlac2 cassette were grown for 72 h on MM containing either 1% fructose with 10 mM L-arabinose and 0.2% yeast extract or 1% xylose and 0.2% yeast extract. The biomass accumulated during growth was nearly equal for all strains. B-galactosidase activity in the culture medium was measured with o-nitrophenyl-β-D-galactoside as a substrate as described in Example 4.

Figure 14:
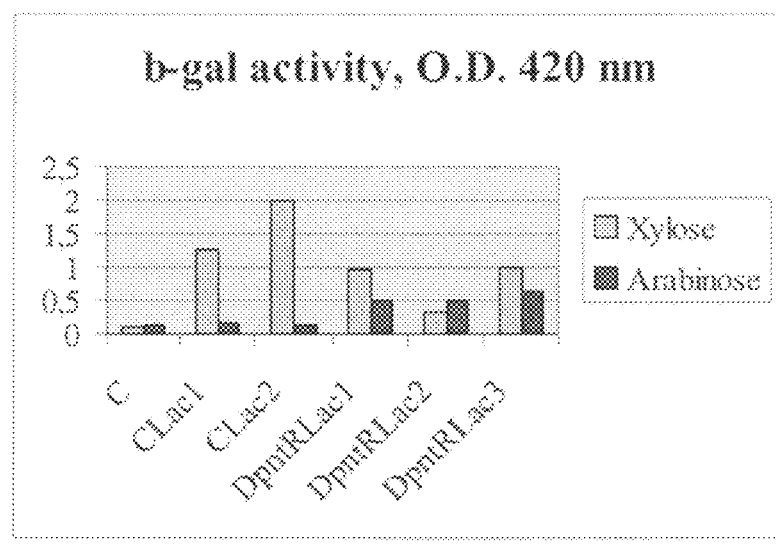
FIG. 14. Extracellular activity of b-galactosidase measured in the culture media of the *A. nidulans* control (CLac1, CLac2) and pntRΔ1 deletant (DpntRLac1, DpntRLac2, DpntRLac3) strains carrying the pExSlac2 expression plasmid. The non-transformed strain (C) served as a control of the endogenous activity. All strains were grown for 3 days on 1% fructose+0.2% YE+10 mM L-arabinose and 1% xylose+0.2% YE. 50 ul of culture samples were used for enzymatic assay. Reactions were run for 10 min at 30° C. Activities are expressed in O.D.
Figure 15:
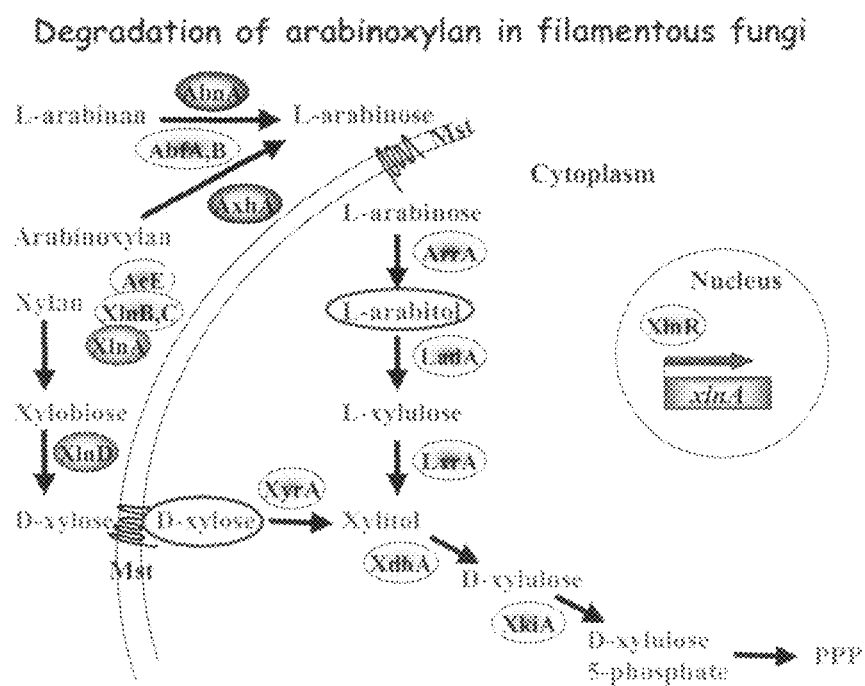
FIG. 15. Shows a schematic of the pathway of degradation of arabinoxylan in filamentous fungi.

As seen in FIG. 14, the endogenous level of b-galactosidase remains negligible in the control *A. nidulans* strain under both growth conditions. As expected, lacA was induced only by D-xylose in the control strain, whereas the pntR deletion resulted, in addition, in the pronounced induction by L-arabinose as well. Variation in the activity level between transformants could be accounted for by a different copy number of the expression vector or sites of its integration. This example shows that the pntR knockout significantly (3-5 fold) improves the L-arabinose-specific expression of the *A. niger* b-galactosidase driven by the heterologous *A. tubingensis* 1M-7 xlnA promoter in the heterologous host *A. nidulans*.

FIG. 14 depicts the extracellular activity of b-galactosidase measured in the culture media of the *A. nidulans* control (CLac1, CLac2) and pntRΔ1 deletant (DpntRLac1, DpntRLac2, DpntRLac3) strains carrying the pExSlac2 expression plasmid. The non-transformed strain (C) served as a control of the endogenous activity. All strains were grown for 3 days on 1% fructose+0.2% YE+10 mM L-arabinose and 1% xylose+0.2% YE. 50 ul of culture samples were used for enzymatic assay. Reactions were run for 10 min at 30° C. Activities are expressed in O.D.

The invention will now be further described by the following numbered paragraphs:

1. An isolated nucleic acid sequence coding for a PntR transcription factor comprising a nucleotide sequence that is the same as, or is complementary to, or contains any suitable codon substitutions for any of those of SEQ ID NOs: 1, 3 or 5 or comprises a sequence which has at least 60% sequence homology with any of SEQ ID NOs: 1, 3 or 5.
2. An isolated nucleic acid sequence according to paragraph 1 which encodes a PntR transcription factor polypeptide comprising the amino acid sequence as shown in any of SEQ ID NOs: 2, 4 or 6 or a sequence having at least 75% identity thereto or an effective fragment thereof.
3. An isolated nucleic acid sequence according to paragraph 2 which is obtained from an *Aspergillus, Trichoderma* or *Penicillium* cell.
4. An isolated nucleic acid sequence according to paragraph 3 which is obtained from an *Aspergillus* cell.
5. A plasmid or expression vector system comprising a nucleic acid sequence according to any of paragraphs 1 to 4.
6. A host cell transformed or transfected with the plasmid or expression vector system of paragraph 5.
7. A polypeptide comprising the amino acid sequence corresponding to *Aspergillus* PntR or a functional equivalent thereof.
8. A polypeptide according to paragraph 7 having the same amino acid sequence or a sequence that is at least 75% identical to that of an *Aspergillus* PntR.
9. A polypeptide according to paragraph 7 or paragraph 8 comprising the amino acid sequence as shown in any of SEQ ID NOs: 2, 4 or 6 or a sequence having at least 75% identity thereto or an effective fragment thereof.
10. A nucleic acid construct arranged to knock down the expression or function of the transcription factor PntR.
11. A nucleic acid construct according to paragraph 10 comprising a nucleic acid sequence encoding a functionally disrupted PntR.
12. A nucleic acid construct according to paragraph 11 comprising a nucleic acid sequence encoding PntR and lacking the region encoding $Zn_2Cy_6$.
13. A nucleic acid construct according to paragraph 10 comprising all or a fragment of a nucleic acid sequence of any of paragraphs 1 to 4.
14. A plasmid or vector system comprising a nucleic acid construct according to any of paragraphs 10 to 13.
15. A method of disrupting PntR expression in a cell comprising introducing a nucleic acid construct as paragraphed in any of paragraphs 10 to 13 or a plasmid or vector system as paragraphed in paragraph 14 into said cell.
16. A host cell transformed or transfected with a nucleic acid construct arranged to knock down the expression or function of the transcription factor PntR as paragraphed in any of paragraphs 10 to 13 or a plasmid or vector system according to paragraph 14.
17. A host cell according to paragraph 16 further comprising a nucleic acid construct comprising a coding sequence of a protein of interest (POI) under the transcriptional control of a promoter regulated by XlnR.
18. A host cell according to paragraph 16 or paragraph 17 wherein said host cell is selected from the group consisting of *Aspergillus* sp., *Trichoderma* and *Penicillium* sp.
19. A host cell according to any of paragraphs 16 to 18 capable of producing an extracellular xylanase.
20. A host cell according to any of paragraphs 16 to 19 wherein said cell is protease-deficient.
21. A host cell according to any of paragraphs 16 to 20 wherein said cell has a block in L-arabinose metabolism.
22. A host cell according to any of paragraphs 16 to 21 wherein said cell exhibits increased xylanase activity.
23. A host cell according to any of paragraphs 16 to 22 wherein said cell is useful for production of a POI.
24. A method of expressing in a host cell a POI whose coding sequence is under the transcriptional control of a promoter regulated by XlnR, said method comprising modulating the transcription factor PntR in said host cell.
25. A method according to paragraph 24 comprising the steps of providing a PntR-deficient host cell comprising the gene encoding the POI under XlnR transcriptional control, and cultivating the host cell under suitable conditions.
26. A method according to any of paragraphs 24 to 25 wherein the PntR has a nucleic acid sequence as set out in any of SEQ ID NOS: 1, 3 or 5 or a sequence having more than 60% identity thereto.
27. A method according to any of paragraphs 24 and 26 comprising using a host cell according to any of paragraphs 16 to 23.
28. A method according to any of paragraphs 24 to 27 wherein the POI is a homologous protein.
29. A method according to any of paragraphs 24 to 27 wherein the POI is a heterologous protein.
30. A method according to any of paragraphs 24 to 29 wherein the host cell is a filamentous fungal cell and, preferably, *Aspergillus, Trichoderma* or *Penicillium* spp.
31. A method according to any of paragraphs 24 to 30 wherein said method of expressing a POI is part of a method of production of said POI and further comprises isolating/purifying said POI.
32. A method of production of a POI comprising expressing in a host cell a POI whose coding sequence is under the transcriptional control of a promoter regulated by XlnR, said method comprising modulating the transcription factor PntR in said host cell.

33. Use of modulation of the transcription factor PntR in the manufacture of a host cell to increase expression of a protein of interest (POI) whose coding sequence is under the transcriptional control of a promoter regulated by XlnR.

REFERENCES

Tilburn J, Scazzocchio C, Taylor G G, Zabicky-Zissman J H, Lockington R A, and Davies R W. (1983). Transformation by integration in *Aspergillus nidulans*. Gene, v.26: 205-221.

Punt P. J. and van den Hondel C. A. M. J. J. (1992). Transformation of filamentous fungi based on hygromycin B and phleomycin resistance markers. Meth. Enzymol., v.216: 447-457.

Sambrook J., Fritsch E. F. and Maniastis T. (1989). Molecular cloning: a laboratory manual, 2$^{nd}$ ed. Cold Spring Harbor Laboratory Press, Cold Spring Harbor, N.Y.

Vishniac W, Santer M. (1957) The *thiobacilli*. Bacteriol. Rev., v.21: 195-213.

Contreras, R., Carrez, D., Kinghorn, J. R. and van den Hondel, C. A. M. J. J. (1991). Efficient kex2-like processing of a glucoamylase-interleukin 6 fusion protein by *Aspergillus nidulans* and secretion of mature interleukin 6. Bio/Technology. v.9: 378-381.

Cove D. (1966) The induction and repression of nitrate reductase in the fungus *Aspergillus nidulans*. Biochem. Biophys. Acta, v.113: 51-56.

Chaveroche M K, Ghigo J M, d'Enfert C. (2000). A rapid method for efficient gene replacement in the filamentous fungus *Aspergillus nidulans*. Nucleic Acids Res., v.28 (22): E97.

Davies, R. W. (1994). Heterologous gene expression and protein secretion in *Aspergillus*. In *Aspergillus:* 50 years on. Edited by S. D. Martinelli and J. R: Kinghorn. v.29: 527-560.

Fidel S, Doonan J H, Morris N R. (1988). *Aspergillus nidulans* contains a single actin gene which has unique intron locations and encodes a gamma-actin. Gene, v.70: 283-93.

Gouka R J, Hessing J G, Punt P J, Stam H, Musters W, Van den Hondel C A. (1996). An expression system based on the promoter region of the *Aspergillus awamori* 1,4-beta-endoxylanase A gene. Appl Microbiol Biotechnol. v.46: 28-35.

Marui J, Kato M, Kobayashi T, Tsukagoshi N. (2003). Upregulation of promoter activity of the *Aspergillus oryzae* xylanase gene by site-directed mutagenesis. Biotechnol Lett. v. 25: 371-4.

de Graaff L H, van den Broeck H C, van Ooijen A J, Visser J. (1994). Regulation of the xylanase-encoding xlnA gene of *Aspergillus tubigensis*. Mol. Microbiol. v. 12: 479-90.

Van den Hombergh, J P T W., van de Vondervoort, P J I., Fraissinet-Tachet, L and Visser J. (1997). *Aspergillus* as a host for heterologous protein production: the problem of proteases. TIBTECH. v.15: 256-263.

Hessing J G, van Rotterdam C, Verbakel J M, Roza M, Maat J, van Gorcom R F, van den Hondel C A. (1994). Isolation and characterization of a 1,4-beta-endoxylanase gene of *A. awamori*. Curr Genet. v.26: 228-32.

Prathumpai W, McIntyre M, Nielsen J. (2004). The effect of CreA in glucose and xylose catabolism in *Aspergillus nidulans*. Appl Microbiol Biotechnol. v. 63: 748-53.

Orejas M, MacCabe A P, Perez-Gonzalez J A, Kumar S, Ramon D. (2001). The wide-domain carbon catabolite repressor CreA indirectly controls expression of the *Aspergillus nidulans* xlnB gene, encoding the acidic endo-beta-(1,4)-xylanase X(24). J. Bacteriol. v. 183: 1517-23.

Gouka R J, Stam H, Fellinger A J, Muijsenberg R J, van de Wijngaard A, Punt P J, Musters W, van den Hondel C A. (1996). Kinetics of mRNA and protein synthesis of genes controlled by the 1,4-beta-endoxylanase A promoter in controlled fermentations of *Aspergillus awamori*. Appl Environ Microbiol. v.62: 3646-9.

Gielkens M M, Dekkers E, Visser J, de Graaff L H. (1999). Two cellobiohydrolase-encoding genes from *Aspergillus niger* require D-xylose and the xylanolytic transcriptional activator XlnR for their expression. Appl Environ Microbiol. v.65: 4340-5.

Hasper A A, Visser J, de Graaff L H. (2000). The *Aspergillus niger* transcriptional activator XlnR, which is involved in the degradation of the polysaccharides xylan and cellulose, also regulates D-xylose reductase gene expression. Mol. Microbiol. v.36: 193-200.

Hasper A A, Trindade L M, van der Veen D, van Ooyen A J, de Graaff L H. (2004). Functional analysis of the transcriptional activator XlnR from *Aspergillus niger*. Microbiology. v. 150: 1367-75.

Johnstone, I. L., Hughes, S. G., and Clutterbuck, A. J. (1985). Cloning an *Aspergillus nidulans* developmental gene by transformation. EMBO J. v.4:1307-11. Nikolaev I, Mathieu M, van de Vondervoort P, Visser J, Felenbok B. (2002). Heterologous expression of the *Aspergillus nidulans* alcR-alcA system in *Aspergillus niger*. Fungal Genet Biol. v.37: 89-97.

Mathieu M, Felenbok B. (1994). The *Aspergillus nidulans* CREA protein mediates glucose repression of the ethanol regulon at various levels through competition with the ALCR-specific transactivator. EMBO J. v.13: 4022-7.

Orejas M, MacCabe A P, Perez Gonzalez J A, Kumar S, Ramon D. (1999). Carbon catabolite repression of the *Aspergillus nidulans* xlnA gene. Mol. Microbiol. v.31: 77-84.

de Vries R P, Visser J, de Graaff L H. (1999). CreA modulates the XlnR-induced expression on xylose of *Aspergillus niger* genes involved in xylan degradation. Res Microbiol. v.150: 281-5.

Xiong H, Turunen O, Pastinen O, Leisola M, von Weymarn N. (2004). Improved xylanase production by *Trichoderma reesei* grown on L-arabinose and lactose or D-glucose mixtures. Appl Microbiol Biotechnol. v.64: 353-8.

MacCabe A P, Orejas M, Perez-Gonzalez J A, Ramon D. (1998). Opposite patterns of expression of two *Aspergillus nidulans* xylanase genes with respect to ambient pH. J. Bacteriol. v.180: 1331-3.

Prathumpai W, Gabelgaard J B, Wanchanthuek P, van de Vondervoort P J, de Groot M J, McIntyre M, Nielsen J. (2003). Metabolic control analysis of xylose catabolism in *Aspergillus*. Biotechnol Prog. v.19: 1136-41.

Rose S H, and van Zyl W H. (2002). Constitutive expression of the *Trichoderma reesei* beta-1,4-xylanase gene (xyn2) and the beta-1,4-endoglucanase (egi) in *Aspergillus niger* in molasses and defined glucose media. Appl. Microbiol. Biotechnol. v.58: 461-8.

Vavilova E A, Antonova S V, Barsukov E D, Vinetskii IuP. (2003). Mechanism of overproduction of secreted enzymes in the mycelial fungus *Penicillium canescens*. Prikl Biokhim Mikrobiol. v.39: 284-92 (russ).

Ward, M., Wilson, L. J., Kodama, K. H., Rey, M. W., and Berka, R. M. (1990). Improved production of chymosin in *Aspergillus* by expression as a glucoamylase-chymosin fusion. Bio/Technology. v.8: 435-438.

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method of expressing in a host cell a protein of interest (POI) whose coding sequence is under the transcriptional control of a promoter regulated by XlnR, said method comprising reducing the expression or activity of the transcription factor pentose regulator (PntR) in said host cell; wherein the PntR is encoded by a nucleic acid sequence as set out in any of SEQ ID NOs: 1, 3 or 5 or a sequence having at least 90% identity thereto; and wherein said host cell is a fungal host cell.

2. A method according to claim 1 comprising the steps of providing a PntR-deficient host cell comprising the gene encoding the POI under XlnR transcriptional control, and cultivating the host cell under suitable conditions.

3. A method according to claim 1 wherein the POI is a homologous protein.

4. A method according to claim 1 wherein the POI is a heterologous protein.

5. A method according to claim 1 wherein said method of expressing a POI is part of a method of production of said POI and further comprises isolating or purifying said POI.

6. A method of production of a POI comprising expressing in a host cell a POI whose coding sequence is under the transcriptional control of a promoter regulated by XlnR, said method comprising reducing the expression or activity of the transcription factor PntR in said host cell; wherein the PntR is encoded by a nucleic acid sequence as set out in any of SEQ ID NOs: 1, 3 or 5 or a sequence having at least 90% identity thereto; and wherein said host cell is a fungal host cell.

7. A method according to claim 1 wherein said method of expressing a POI is part of a method of production of said POI and further comprises isolating and purifying said POI.

8. The method according to claim 1 wherein the PntR is encoded by a nucleic acid sequence having at least 95% identity to the sequence as set out in any of SEQ ID NOs: 1, 3 or 5.

9. The method according to claim 6 wherein the PntR is encoded by a nucleic acid sequence having at least 95% identity to the sequence as set out in any of SEQ ID NOs: 1, 3 or 5.

10. A method according to claim 1 wherein the host cell is an *Aspergillus* host cell.

11. A method according to claim 6 wherein the host cell is an *Aspergillus* host cell.

12. A method according to claim 8 wherein the host cell is an *Aspergillus* host cell.

13. A method according to claim 9 wherein the host cell is an *Aspergillus* host cell.

* * * * *

```
                            SEQUENCE LISTING

<160> NUMBER OF SEQ ID NOS: 33

<210> SEQ ID NO 1
<211> LENGTH: 2514
<212> TYPE: DNA
<213> ORGANISM: Aspergillus nidulans

<400> SEQUENCE: 1
atggcatcct cccaccaggg gaacgggaca gtccccaact ctcagaccga cgcaccccg       60 gattcctcca caaagcgccg atggaggcgc aaccgtatag cttgtgactc ttgtcatgct    120
cgccgcgttc gatgcgaccg ccagtttccg tgctcgcgct gcctccgtag cgagatcacc    180
tgcgaattca cgcgcgagcg tcgtaagcga ggccgtatcg cacgatccaa gctggccgaa    240
atggcaaaga acaaaatgga gaccagtgag acgccggctc cggctaagac catgaatggt    300
ataccggcgc ccgctggtac agagatccca gggcatgtct cccccgcatc gactttccac    360
catcgatcgc cgccggcaaa tgctcctact gtttctgctc caagtgttga tggccgacgg    420
tctcagactg acccacaact tcccgtccgg agaccagaaa tcggcgggaa tgttactgag    480
gaatggctcg ccgggacgca tgtatcacca ggatcatacg agttcttgaa tggaccagct    540
tttggagaag gactaggacc gtttcctcac atgttcgatg tatggaacgg tgtcgacctg    600
gccgcctaca gcgctgggac ttcgcaaggg tcgaaagcga ccaacgcgcc gtcaacctct    660
acagcaccgt tgaagtaccc ggttctacag cccttgatgc cgttcgtgga ggcgactctg    720
cctcgaaaac tggtctttga cctgcttgat ctatatttca ccagcgcgtt ttcaactcac    780
atgcaccccg tatgccatca tattcattgc tatgtgctgc ggaaggtttc cttcctcagc    840
aaagatgcgc cacgacccag cagtccggca ctgctttcga gtatgctctg ggtagctgct    900
ctggatgata gggcgttttc gttgccgatt tcgcctccgc agcggaaaag gatctgccaa    960
tttctctgcg ctctcactat ccgcttgttg cgaccgttga ttcatgtttc cttcaaagat   1020
cagggcggcg ccgcagcagc ggttgcagca gcggccgcgg cggccaccaa taacccagcg   1080
ttcgccggcg tcggccagga tctaccgccc actactgtgc accatccgtt tgaaggagga   1140
ggagacgata gaggcctggt agggccggca ggctcgcttg acgatgtgat tacctacatc   1200
catgtagctt ctatcatctc gtccagtgag cagaaggcag ccagtatgcg atggtggcat   1260
gcggccttca ccctagcgcg agagctcaag ctaaatcaag gatcgaggt gatgccgaat    1320 ggcgactccc aagtggaagg gtcaagtccg ccgttcggat actctctacc cggctgggat   1380
ggggctgacc cgggccccgt ctttaattac tcaaacccaa ctcggtccag tctcaattgc   1440
gtctgtgatc gccaggacca gaacaccatc accgaagagc accgcgaaga acggcggcgg   1500
acatggtggc ttctgtacat catggaccgc catctcgcac tgtgctacaa ccggccgttg   1560
gccttgctgg atgccgaaag cgaagactta ctactaccgc tggacgaggc atcctggcag   1620
tcagggatca tacacagtaa cagcccgaag tcggatgggc cgcaatgcct actctctgcc   1680
gacaagaaca agcgtcgcct gtttccgaac ttcatctgcc atgatcattc tgtgtttggc   1740
tttttccttc ccctcatgac gatcaccggc gaactcattg acctgaacca agcgaggaac   1800
```

```
catccgatgc ttggcatgcg actaaacggc aaggacgcgt ggaatgtcca tgtaagcgaa    1860
gttctacgcc agctcgagat ctacaaggct agcttaacca cgttcgccgc tactacatcc    1920
gatccggaag cgccgctgtc cgcttatgcg cacgcccaat ccgaacatct accagccgag    1980
ccatccctct cgcaagcata cgcatggcac acgcaaactg tcatatcgta tgcatcatac    2040
ctggtccacg tgctccacat cctgttggtg ggcaaatggg atcccgtatc cctgatcgag    2100
gacaaagatt tctggacctc ctcccccgca ttcgcatcga ccatctcgca tgcgctggac    2160
gcagccgact cggtcgatca gattctccga tacgacccag acattagttt catgccctat    2220
ttctttggca ttcagttgct gcaaggcagt tttcttctcc tgctgatcgt tgagaggctg    2280
cagaaggaag cgggcgaagg aatccttaat gcatgcgagg tgatgatccg agctacggaa    2340
tcttgtgtgg tgactctgaa caccgaatac cagcgaaatt ccggcaggt catgcgcagt    2400 gccgttgccc aagcacgagg gaggccagtc aatcacagcg agattcgcca ccggcgcaag    2460
gctgtgctag cgctgtaccg gtggacaagg aagggaaccg ggttggctct ctag          2514
```

<210> SEQ ID NO 2
<211> LENGTH: 837
<212> TYPE: PRT
<213> ORGANISM: Aspergillus nidulans

<400> SEQUENCE: 2

```
Met Ala Ser Ser His Gln Gly Asn Gly Thr Val Pro Asn Ser Gln Thr
1               5                   10                  15

Asp Ala Pro Pro Asp Ser Ser Thr Lys Arg Arg Trp Arg Arg Asn Arg
            20                  25                  30

Ile Ala Cys Asp Ser Cys His Ala Arg Arg Val Arg Cys Asp Arg Gln
        35                  40                  45

Phe Pro Cys Ser Arg Cys Leu Arg Ser Glu Ile Thr Cys Glu Phe Thr
    50                  55                  60

Arg Glu Arg Arg Lys Arg Gly Arg Ile Ala Arg Ser Lys Leu Ala Glu
65                  70                  75                  80

Met Ala Lys Asn Lys Met Glu Thr Ser Glu Thr Pro Ala Pro Ala Lys
                85                  90                  95

Thr Met Asn Gly Ile Pro Ala Pro Ala Gly Thr Glu Ile Pro Gly His
            100                 105                 110

Val Ser Pro Ala Ser Thr Phe His His Arg Ser Pro Pro Ala Asn Ala
        115                 120                 125

Pro Thr Val Ser Ala Pro Ser Val Asp Gly Arg Ser Gln Thr Asp
    130                 135                 140

Pro Gln Leu Pro Val Arg Arg Pro Glu Ile Gly Gly Asn Val Thr Glu
145                 150                 155                 160

Glu Trp Leu Ala Gly Thr His Val Ser Pro Gly Ser Tyr Glu Phe Leu
                165                 170                 175

Asn Gly Pro Ala Phe Gly Glu Gly Leu Gly Phe Pro His Met Phe
            180                 185                 190

Asp Val Trp Asn Gly Val Asp Leu Ala Ala Tyr Ser Ala Gly Thr Ser
        195                 200                 205

Gln Gly Ser Lys Ala Thr Asn Ala Pro Ser Thr Ser Thr Ala Pro Leu
    210                 215                 220

Lys Tyr Pro Val Leu Gln Pro Leu Met Pro Phe Val Glu Ala Thr Leu
225                 230                 235                 240

Pro Arg Lys Leu Val Phe Asp Leu Leu Asp Leu Tyr Phe Thr Ser Ala
                245                 250                 255
```

-continued

Phe Ser Thr His Met His Pro Val Cys His His Ile His Cys Tyr Val
                260                 265                 270

Leu Arg Lys Val Ser Phe Leu Ser Lys Asp Ala Pro Arg Pro Ser Ser
            275                 280                 285

Pro Ala Leu Leu Ser Ser Met Leu Trp Val Ala Ala Leu Asp Asp Arg
        290                 295                 300

Ala Phe Ser Leu Pro Ile Ser Pro Gln Arg Lys Arg Ile Cys Gln
305                 310                 315                 320

Phe Leu Cys Ala Leu Thr Ile Arg Leu Leu Arg Pro Leu Ile His Val
                325                 330                 335

Ser Phe Lys Asp Gln Gly Gly Ala Ala Ala Val Ala Ala Ala Ala
            340                 345                 350

Ala Ala Ala Thr Asn Asn Pro Ala Phe Ala Gly Val Gly Gln Asp Leu
                355                 360                 365

Pro Pro Thr Thr Val His His Pro Phe Glu Gly Gly Gly Asp Asp Arg
        370                 375                 380

Gly Leu Val Gly Pro Ala Gly Ser Leu Asp Asp Val Ile Thr Tyr Ile
385                 390                 395                 400

His Val Ala Ser Ile Ile Ser Ser Ser Glu Gln Lys Ala Ala Ser Met
                405                 410                 415

Arg Trp Trp His Ala Ala Phe Thr Leu Ala Arg Glu Leu Lys Leu Asn
            420                 425                 430

Gln Glu Ile Glu Val Met Pro Asn Gly Asp Ser Gln Val Glu Gly Ser
        435                 440                 445

Ser Pro Pro Phe Gly Tyr Ser Leu Pro Gly Trp Asp Gly Ala Asp Pro
        450                 455                 460

Gly Pro Val Phe Asn Tyr Ser Asn Pro Thr Arg Ser Ser Leu Asn Cys
465                 470                 475                 480

Val Cys Asp Arg Gln Asp Gln Asn Thr Ile Thr Glu Glu His Arg Glu
                485                 490                 495

Glu Arg Arg Arg Thr Trp Trp Leu Leu Tyr Ile Met Asp Arg His Leu
            500                 505                 510

Ala Leu Cys Tyr Asn Arg Pro Leu Ala Leu Leu Asp Ala Glu Ser Glu
        515                 520                 525

Asp Leu Leu Leu Pro Leu Asp Glu Ala Ser Trp Gln Ser Gly Ile Ile
        530                 535                 540

His Ser Asn Ser Pro Lys Ser Asp Gly Pro Gln Cys Leu Leu Ser Ala
545                 550                 555                 560

Asp Lys Asn Lys Arg Arg Leu Phe Pro Asn Phe Ile Cys His Asp His
                565                 570                 575

Ser Val Phe Gly Phe Leu Pro Leu Met Thr Ile Thr Gly Glu Leu
            580                 585                 590

Ile Asp Leu Asn Gln Ala Arg Asn His Pro Met Leu Gly Met Arg Leu
        595                 600                 605

Asn Gly Lys Asp Ala Trp Asn Val His Val Ser Glu Val Leu Arg Gln
        610                 615                 620

Leu Glu Ile Tyr Lys Ala Ser Leu Thr Thr Phe Ala Ala Thr Thr Ser
625                 630                 635                 640

Asp Pro Glu Ala Pro Leu Ser Ala Tyr Ala His Ala Gln Ser Glu His
                645                 650                 655

Leu Pro Ala Glu Pro Ser Leu Ser Gln Ala Tyr Ala Trp His Thr Gln
            660                 665                 670

Thr Val Ile Ser Tyr Ala Ser Tyr Leu Val His Val Leu His Ile Leu

```
                    675                 680                 685
Leu Val Gly Lys Trp Asp Pro Val Ser Leu Ile Glu Asp Lys Asp Phe
    690                 695                 700

Trp Thr Ser Ser Pro Ala Phe Ala Ser Thr Ile Ser His Ala Leu Asp
705                 710                 715                 720

Ala Ala Asp Ser Val Asp Gln Ile Leu Arg Tyr Asp Pro Asp Ile Ser
                725                 730                 735

Phe Met Pro Tyr Phe Phe Gly Ile Gln Leu Leu Gln Gly Ser Phe Leu
            740                 745                 750

Leu Leu Leu Ile Val Glu Arg Leu Gln Lys Glu Ala Gly Glu Gly Ile
        755                 760                 765

Leu Asn Ala Cys Glu Val Met Ile Arg Ala Thr Glu Ser Cys Val Val
        770                 775                 780

Thr Leu Asn Thr Glu Tyr Gln Arg Asn Phe Arg Gln Val Met Arg Ser
785                 790                 795                 800

Ala Val Ala Gln Ala Arg Gly Arg Pro Val Asn His Ser Glu Ile Arg
                805                 810                 815

His Arg Arg Lys Ala Val Leu Ala Leu Tyr Arg Trp Thr Arg Lys Gly
            820                 825                 830

Thr Gly Leu Ala Leu
        835

<210> SEQ ID NO 3
<211> LENGTH: 2335
<212> TYPE: DNA
<213> ORGANISM: Aspergillus niger
<220> FEATURE:
<221> NAME/KEY: modified_base
<222> LOCATION: (2323)..(2323)
<223> OTHER INFORMATION: a, c, t or g

<400> SEQUENCE: 3
tcttcgcagt gatatccggt gtgaattcac tcgcgaacga cgaaagagag gacgcattgc      60
gcgatcccga ctggtagaga ccaagactgc tgtagagaag gcgagccagc ctgtggagac     120
tcgagattca gcaccggcac ctgcagaagc agggtctggc ccagttccaa atggctctcc     180
ttcctcaaca tttcaccata gatcgccggc gacaaatgat gtgacggggt cggccccaag     240
tatcgacgag cggcgctctc aagcggatgt atcacttcct cccagaaagt cagggcacac     300
tgttaatgcg acagaggaat ggctagcagg cacgcatgtc tctccaggat cctatgagcc     360
cttggcaggc atcggccccg agaaggccc tttccctcga atctttgata tctggaatgg     420
ggtcgacttg gccggttata gcgacccagc atctcaaggc tccaagataa caggccttgg     480
tcagacacca gcaccatctg caacgatcct aaagtatccg gtcctccagc cagtaatgcc     540
ctatctggaa tcgagcttgc ctcgaaagct agtatacgac cttctcgacc tgtactttac     600
aagcgcgttt tccacacata tgcatcctgt gtgccatcac attcattgct atgtcctacg     660
aaaggcgtct tttctaagcc gagaggctcc tcgacctagc agcccggcac ttctggccag     720
tatgctttgg gtggcagcgt tagatgatcg tgcgtttgct ttgccgatat ctccacccca     780
gagaaagaaa atatgtcagt tcttgtgtgc tctaacatta cgacttttgc gaccgttgat     840
tcacgtgtca ttcaaagagc aagaaggcgc cgccgcgagt gacccacttc atgctgcggt     900
cggtcaggat ggccctccta caaccgtgca ccaccgtttt gaggtcggtg gtgatgatcg     960
ggggttagtt ggccctgcag gatcattgga cgatgttatc acatacatcc atgtggcatc    1020
catcatctcc tcaagcgagc aaaaggccgc cagcatgcga tggttcgttt ttgttcaagt    1080
```

-continued

```
aacttgaggc gagcacggaa gctaaccaat cttaggtggc atgccgcctt tactcttgca    1140
cgagaattga agctgaatca ggagatcgag gtgatgccca gtgaggagaa tcacccagag    1200
ggttcgagcc cgtcatttga ttattcactt gcgggatgga gtggcgtgga cacgggcccc    1260
ttttttgatt attcaaaccc tgcccggcca agcttgaatt gcgtatgcga ccgtggccac    1320
gaactgcgtg gcgctatcac cgaagagcat cgtgaagagc gtcgtcggac atggtggctc    1380
ctctacatta tggaccgtca cctcgctctc tgctacaatc gccccttgc tctactcgat     1440 gctgaaagcg aggatctctt attgcctctg gacgaagggt catggcagtc aggtaatatc    1500
cacagcaata gtcccaaccc ggacggacca cagtgcccac tgtcaggcga agaacaag     1560 cgccgcgttt ccctaatttt catctgccat gatcattcta tcttcggctt ctttctccct   1620
ctgatgacca ttactggtga attaatcgac ctgaaccaag ctcggaacca tccaatgctt    1680
ggagcacgct tgaacggaaa ggaccccctgg gatgcgcacg ttggtgaagt actacgccag    1740
cttgagcttt acaaggctag tctcactacg tttgcagcca ctgcgtcgga tcccgatgcg    1800
cccttgtcca gtgccttccc ccctaaaccc gatcaacaac cagttgaacc ctcactcgcc    1860
caggcttatt catggcatac tcaaacggtc atctcgtatg catcctacct cgtgcatgtg    1920
ctgcatattc ttcttgttgg caaatgggat cctgtgtcgt tgatcgagga taaggacttc    1980
tggacttcat cgcctgcatt cgcctccacc atctctcacg ctcttgatgc ggcagactca    2040
gtggaccata tcttacgcta cgaccccgat attagtttta tgccgtattt cttcggcatt    2100
caattgctcc aaggcagctt tcttctcctg ctgattgtgg agcggctgca gaaagaagcg    2160
ggggagggta ttctaaatgc ctgcgaggtg atgattcgag cgaccgagtc ctgcgtggtg    2220
acgttgaaca ctgaatatca acggaacttc cgacaggtca tgcggagcgc cgttgcgcag    2280
gcgcgtgggc gccctgtcaa tcacagtgag atccggcatc gtngcaaggc cgtct         2335
```

<210> SEQ ID NO 4
<211> LENGTH: 760
<212> TYPE: PRT
<213> ORGANISM: Aspergillus niger
<220> FEATURE:
<221> NAME/KEY: MOD_RES
<222> LOCATION: (757)..(757)
<223> OTHER INFORMATION: Any naturally occurring amino acid

<400> SEQUENCE: 4

```
Leu Arg Ser Asp Ile Arg Cys Glu Phe Thr Arg Glu Arg Arg Lys Arg
1               5                   10                  15

Gly Arg Ile Ala Arg Ser Arg Leu Val Glu Thr Lys Thr Ala Val Glu
            20                  25                  30

Lys Ala Ser Gln Pro Val Glu Thr Arg Asp Ser Ala Pro Ala Pro Ala
        35                  40                  45

Glu Ala Gly Ser Gly Pro Val Pro Asn Gly Ser Pro Ser Ser Thr Phe
    50                  55                  60

His His Arg Ser Pro Ala Thr Asn Asp Val Thr Gly Ser Ala Pro Ser
65                  70                  75                  80

Ile Asp Glu Arg Arg Ser Gln Ala Asp Val Ser Leu Pro Pro Arg Lys
                85                  90                  95

Ser Gly His Thr Val Asn Ala Thr Glu Glu Trp Leu Ala Gly Thr His
            100                 105                 110

Val Ser Pro Gly Ser Tyr Glu Pro Leu Ala Gly Ile Gly Pro Gly Glu
        115                 120                 125

Gly Pro Phe Pro Arg Ile Phe Asp Ile Trp Asn Gly Val Asp Leu Ala
    130                 135                 140
```

-continued

```
Gly Tyr Ser Asp Pro Ala Ser Gln Gly Ser Lys Ile Thr Gly Leu Gly
145                 150                 155                 160

Gln Thr Pro Ala Pro Ser Ala Thr Ile Leu Lys Tyr Pro Val Leu Gln
            165                 170                 175

Pro Val Met Pro Tyr Leu Glu Ser Leu Pro Arg Lys Leu Val Tyr
        180                 185                 190

Asp Leu Leu Asp Leu Tyr Phe Thr Ser Ala Phe Ser Thr His Met His
            195                 200                 205

Pro Val Cys His His Ile His Cys Tyr Val Leu Arg Lys Ala Ser Phe
        210                 215                 220

Leu Ser Arg Glu Ala Pro Arg Pro Ser Ser Pro Ala Leu Leu Ala Ser
225                 230                 235                 240

Met Leu Trp Val Ala Ala Leu Asp Asp Arg Ala Phe Ala Leu Pro Ile
                245                 250                 255

Ser Pro Pro Gln Arg Lys Lys Ile Cys Gln Phe Leu Cys Ala Leu Thr
            260                 265                 270

Leu Arg Leu Leu Arg Pro Leu Ile His Val Ser Phe Lys Glu Gln Glu
        275                 280                 285

Gly Ala Ala Ser Asp Pro Leu His Ala Ala Val Gly Gln Asp Gly
        290                 295                 300

Pro Pro Thr Thr Val His His Pro Phe Glu Val Gly Gly Asp Asp Arg
305                 310                 315                 320

Gly Leu Val Gly Pro Ala Gly Ser Leu Asp Asp Val Ile Thr Tyr Ile
                325                 330                 335

His Val Ala Ser Ile Ile Ser Ser Ser Glu Gln Lys Ala Ala Ser Met
                340                 345                 350

Arg Trp Trp His Ala Ala Phe Thr Leu Ala Arg Glu Leu Lys Leu Asn
            355                 360                 365

Gln Glu Ile Glu Val Met Pro Ser Glu Glu Asn His Pro Glu Gly Ser
        370                 375                 380

Ser Pro Ser Phe Asp Tyr Ser Leu Ala Gly Trp Ser Gly Val Asp Thr
385                 390                 395                 400

Gly Pro Phe Phe Asp Tyr Ser Asn Pro Ala Arg Pro Ser Leu Asn Cys
                405                 410                 415

Val Cys Asp Arg Gly His Glu Leu Arg Gly Ala Ile Thr Glu Glu His
            420                 425                 430

Arg Glu Glu Arg Arg Arg Thr Trp Trp Leu Leu Tyr Ile Met Asp Arg
        435                 440                 445

His Leu Ala Leu Cys Tyr Asn Arg Pro Leu Ala Leu Leu Asp Ala Glu
    450                 455                 460

Ser Glu Asp Leu Leu Pro Leu Asp Glu Gly Ser Trp Gln Ser Gly
465                 470                 475                 480

Asn Ile His Ser Asn Ser Pro Asn Pro Asp Gly Pro Gln Cys Pro Leu
                485                 490                 495

Ser Gly Glu Lys Asn Lys Arg Arg Val Phe Pro Asn Phe Ile Cys His
            500                 505                 510

Asp His Ser Ile Phe Gly Phe Phe Leu Pro Leu Met Thr Ile Thr Gly
        515                 520                 525

Glu Leu Ile Asp Leu Asn Gln Ala Arg Asn His Pro Met Leu Gly Ala
        530                 535                 540

Arg Leu Asn Gly Lys Asp Pro Trp Asp Ala His Val Gly Glu Val Leu
545                 550                 555                 560

Arg Gln Leu Glu Leu Tyr Lys Ala Ser Leu Thr Thr Phe Ala Ala Thr
```

```
                565                 570                 575
Ala Ser Asp Pro Asp Ala Pro Leu Ser Ser Ala Phe Pro Pro Lys Pro
            580                 585                 590

Asp Gln Gln Pro Val Glu Pro Ser Leu Ala Gln Ala Tyr Ser Trp His
            595                 600                 605

Thr Gln Thr Val Ile Ser Tyr Ala Ser Tyr Leu Val His Val Leu His
            610                 615                 620

Ile Leu Leu Val Gly Lys Trp Asp Pro Val Ser Leu Ile Glu Asp Lys
625                 630                 635                 640

Asp Phe Trp Thr Ser Pro Ala Phe Ala Ser Thr Ile Ser His Ala
                645                 650                 655

Leu Asp Ala Ala Asp Ser Val Asp His Ile Leu Arg Tyr Asp Pro Asp
            660                 665                 670

Ile Ser Phe Met Pro Tyr Phe Phe Gly Ile Gln Leu Gln Gly Ser
                675                 680                 685

Phe Leu Leu Leu Leu Ile Val Glu Arg Leu Gln Lys Glu Ala Gly Glu
            690                 695                 700

Gly Ile Leu Asn Ala Cys Glu Val Met Ile Arg Ala Thr Glu Ser Cys
705                 710                 715                 720

Val Val Thr Leu Asn Thr Glu Tyr Gln Arg Asn Phe Arg Gln Val Met
                725                 730                 735

Arg Ser Ala Val Ala Gln Ala Arg Gly Arg Pro Val Asn His Ser Glu
            740                 745                 750

Ile Arg His Arg Xaa Lys Ala Val
            755                 760

<210> SEQ ID NO 5
<211> LENGTH: 3914
<212> TYPE: DNA
<213> ORGANISM: Aspergillus tubingensis
<220> FEATURE:
<221> NAME/KEY: modified_base
<222> LOCATION: (3858)..(3858)
<223> OTHER INFORMATION: a, c, t or g

<400> SEQUENCE: 5
gcggcctatt agtgacaaac cagagtttgc caccagggca gtgaaccctg gagagctccc      60
catgtgtggc ccggctctgg attagggccc ttttttagcg cgtgcggagt ccagccccga     120
cggtttcccc gcgatggatc gcttctgctc tgcccggcct gttttgcgct ctgccactca     180
gctcccttct tcctccatgg aaaagtcctc tcctctgctc tacgggtttt tatccgcatt     240
gcgtcttgtt aacggcgcat cctagaaggc ttagcggtcg tcgtgggtac gtatgtcaag     300
ccagttactc atcaacaact gcctcggtct ctttccccgc ttgtaattgc ctggtaaggg     360
ctaaggaccg gttctttcgc tcctttcgtc ttggccggtt gctgacttct caaccccatt     420
tttttcagac tgcgattctt ttgcataccc tcatatacct ctggaatcgc caatgtcggc     480
ctgaaatgga tactgcccag tcggggacg cccaggcatc cagcgttcca gcagccaccg     540
aagaaccaac cggcggagcc tcaacaaaac gtcgttggag aaggaatcgg atagcttgcg     600
actcctgcca ttcgcgtcgc gtgcggtgcg atcgagcctt ccctgctcg cgctgccttc     660 gcagtgaaat ccgatgcgag ttcactcggg aacgacgcaa gcgaggacgc attgcgcgat     720
cccgactggt agagcccaat gctgccactg aaaagccgac caaacctgtg gagtcccaag     780
ccgcagcacc ggcacctgcg gaagcaggat ctggtccggt tccaaatggc tctccctcta     840
cgacttttcg ccatagatcg ccagcgacaa atgatgtgac ggtgtcagcc ccaagtattg     900
```

```
acgagcggcg ctctcaggcg gatgtgtcac ttcctcccag gaagtcaggg catacagtta    960
atgcgacaga ggaatggcta gcaggcacgc atgtctctcc aggttcctat gagcccttgg   1020
caggcatcgg ccctggggaa ggccttttc ctcggatctt tgatatctgg aatggggttg    1080
acctggccgg ttacagtgat ccagcatctc agggttccaa gataaccggc cttggacaga   1140
caccagcacc gtctgcaaca atcctaaaat atccagtact ccagccagta atgccatatt   1200
tggagtcgag cttgcctcga aagctagtat acgatcttct cgacctgtac ttcacaagcg   1260
cattctccac gcatatgcat cccgtgtgtc atcacatcca ctgctatgtt ctacgaaagg   1320
catcatttct gagccgggaa gcccctcggc ctagcagccc tgcacttctg gccagcatgc   1380
tttgggtggc agcgttagat gaccgtgcgt ttgctttgcc gatatctcct ccccagagga   1440
agaagatatg tcaatttta tgtgctctaa cgttacggct cttgcgaccg ttggttcacg    1500
tgtcattcaa agagcaagag ggcgccgcgg cgagcgaccc acttcatgct gcgatcggtc   1560
aggacggtcc ccctacaacg gtgcaccacc catttgaagc cggtggtgat gatcgggggc   1620
tggtcggccc tgcaggatca ttggacgatg tcatcacata catccatgta gcatccatta   1680
tctcttcaag cgaacaaaag gccgccagca tgcgatggtt cgtttattc aagttacccg    1740
aagcgagcaa ggaagctaac caatcttagg tggcatgccg cctttactct tgcacgggaa   1800
ctgaagctca atcaggagat cgaggtgatg cctagtgagg agaatcaccc agagggctcg   1860
agcccgtcat ttgattattc acttgcggga tggagtggcg ttgacacggg ccccttttc    1920
gattattcaa accctgctcg gccaagcttg aattgcgtat gcgaccgtgg ccacgaattg   1980
cgtggcgcta ttaccgaaga gcaccgtgaa gagcgtcgtc ggacatggtg gcttctctac   2040
atcatggacc gtcacctcgc tctctgctac aatcgccccc ttgctctact cgatgctgaa   2100
agcgaggatc ttttattgcc gctggacgaa gggtcatggc agtctgggaa catccacagc   2160
aatagtccca aaccggatgg accacagtgc ccgctgtcag gcgagaagaa caaacgccgc   2220
gttttcccca atttcatttg ccatgaccac tctatcttcg gcttcttcct gcctctcatg   2280
accattactg gcgaattaat cgacttaaac caagctcgta accatccgat gcttggagca   2340
cgcttgaatg gaaaggacgc ctgggatgcg cacgtcggtg aagtgctgcg ccagcttgag   2400
ctttacaagg ctagtctcac aacgtttgct gccactgcgt cggatcccga tgcgccctta   2460
tccagtgcct tcccctaa acccgatcag caaccagtcg agccctcact cgcccaggct     2520
tattcatggc atactcaaac ggtcatctcg tatgcatcct atcttgtgca tgtgctacat   2580
attcttcttg tcgggaaatg ggatcctgtg tcgttgatcg aagataagga cttctggact   2640
tcatcgcccg cgttcgcctc caccatctct cacgcccttg atgcggcaga ctcggtggac   2700
catatcctac gttacgaccc cgatatcagt tttatgccgt attcttcgg catccaatta    2760
cttcaaggca gctttcttct cttgctgatt gtagagcggc tgcagaaaga agcggggag    2820
ggtattctga atgcgtgcga ggtgatgatc cgagcgaccg agtcctgtgt ggtgacgttg   2880
aacactgaat accaacgaaa ctttcgacag gtcatgcgga gcgctgttgc gcaggcgcgt   2940
gggcgccctg tcaatcacag cgagatccgg catcgtcgca aggccgtctt agcactctac   3000
cggtggaccc ggaagggcac tgggttggcc ctttagattt agagtttctc acagcgccga   3060
tgcccatttc agcgcacggt tgcatcggct ccgcatccgc aggccatcgg ctggagagag   3120
cttaaatcat ctcccgccag ggcatgcttg gttctaggcc agtcgcagag actggcatat   3180
gcaggcacag tatcccctcc ctctcggttg attaccttgc ctgaacgggc tcgctccagc   3240
tcgcctctat ggctcattgc ccggtgcctg catctgccgg accttacccc ggcattggca   3300
```

```
attgatcgca acggctgctg ctattagccc aaagtatctc gtagtattta ttattttttt    3360
ttggatactg ctctccgatg ttaccctgta catatacgag catttatgct gttttttggtg   3420 tctctggctt gtttgttctg actcgcgggt tttaatctac caaacggttt tttcttcttc   3480
tggacaccac ctcccgaatg ccatgcccct ttcctcctaa caaagcaaac atcgcttcta   3540
ggcatagacc gtcgctaaag tcgggcatcg catgattctg cacttggtgc aaggaccggg   3600
gttgttgggc ggccccttcc ccttacccca gatttaacga acgggccgtg ctcgctcggt   3660
ccgaacctgg gtctttcggt taaattctta aaaaaccgaa gccgttgcgg ggagaaaagc   3720
cattgcattg ggaatcgaac caacaggcgc tcagctttaa cagcctttaa ttcccgtagt   3780
tcggcaggcc ggggagggtg ctcggttaat tgccacacca gaatatgggg tatgcaaggt   3840
tcagcgacac cacatggncc ccgtgaagat cagatggttc ctggtccgtc aaatcactga   3900
gcttccctcg aggg                                                     3914
```

<210> SEQ ID NO 6
<211> LENGTH: 832
<212> TYPE: PRT
<213> ORGANISM: Aspergillus tubingensis

<400> SEQUENCE: 6

```
Met Asp Thr Ala Gln Ser Gly Asp Ala Gln Ala Ser Ser Val Pro Ala
1               5                   10                  15

Ala Thr Glu Glu Pro Thr Gly Gly Ala Ser Thr Lys Arg Arg Trp Arg
            20                  25                  30

Arg Asn Arg Ile Ala Cys Asp Ser Cys His Ser Arg Arg Val Arg Cys
        35                  40                  45

Asp Arg Ala Phe Pro Cys Ser Arg Cys Leu Arg Ser Glu Ile Arg Cys
    50                  55                  60

Glu Phe Thr Arg Glu Arg Arg Lys Arg Gly Arg Ile Ala Arg Ser Arg
65                  70                  75                  80

Leu Val Glu Pro Asn Ala Ala Thr Glu Lys Pro Thr Lys Pro Val Glu
                85                  90                  95

Ser Gln Ala Ala Ala Pro Ala Pro Ala Glu Ala Gly Ser Gly Pro Val
            100                 105                 110

Pro Asn Gly Ser Pro Ser Thr Thr Phe Arg His Arg Ser Pro Ala Thr
        115                 120                 125

Asn Asp Val Thr Val Ser Ala Pro Ser Ile Asp Glu Arg Arg Ser Gln
    130                 135                 140

Ala Asp Val Ser Leu Pro Pro Arg Lys Ser Gly His Thr Val Asn Ala
145                 150                 155                 160

Thr Glu Glu Trp Leu Ala Gly Thr His Val Ser Pro Gly Ser Tyr Glu
                165                 170                 175

Pro Leu Ala Gly Ile Gly Pro Gly Glu Gly Pro Phe Pro Arg Ile Phe
            180                 185                 190

Asp Ile Trp Asn Gly Val Asp Leu Ala Gly Tyr Ser Asp Pro Ala Ser
        195                 200                 205

Gln Gly Ser Lys Ile Thr Gly Leu Gly Gln Thr Pro Ala Pro Ser Ala
    210                 215                 220

Thr Ile Leu Lys Tyr Pro Val Leu Gln Pro Val Met Pro Tyr Leu Glu
225                 230                 235                 240

Ser Ser Leu Pro Arg Lys Leu Val Tyr Asp Leu Leu Asp Leu Tyr Phe
                245                 250                 255

Thr Ser Ala Phe Ser Thr His Met His Pro Val Cys His His Ile His
            260                 265                 270
```

```
Cys Tyr Val Leu Arg Lys Ala Ser Phe Leu Ser Arg Glu Ala Pro Arg
            275                 280                 285

Pro Ser Ser Pro Ala Leu Leu Ala Ser Met Leu Trp Val Ala Ala Leu
        290                 295                 300

Asp Asp Arg Ala Phe Ala Leu Pro Ile Ser Pro Gln Arg Lys Lys
305                 310                 315                 320

Ile Cys Gln Phe Leu Cys Ala Leu Thr Leu Arg Leu Leu Arg Pro Leu
                325                 330                 335

Val His Val Ser Phe Lys Glu Gln Glu Gly Ala Ala Ala Ser Asp Pro
            340                 345                 350

Leu His Ala Ala Ile Gly Gln Asp Gly Pro Thr Thr Val His His
        355                 360                 365

Pro Phe Glu Ala Gly Gly Asp Asp Arg Gly Leu Val Gly Pro Ala Gly
    370                 375                 380

Ser Leu Asp Asp Val Ile Thr Tyr Ile His Val Ala Ser Ile Ile Ser
385                 390                 395                 400

Ser Ser Glu Gln Lys Ala Ala Ser Met Arg Trp Trp His Ala Ala Phe
                405                 410                 415

Thr Leu Ala Arg Glu Leu Lys Leu Asn Gln Ile Glu Val Met Pro
            420                 425                 430

Ser Glu Glu Asn His Pro Glu Gly Ser Ser Pro Ser Phe Asp Tyr Ser
        435                 440                 445

Leu Ala Gly Trp Ser Gly Val Asp Thr Gly Pro Phe Phe Asp Tyr Ser
    450                 455                 460

Asn Pro Ala Arg Pro Ser Leu Asn Cys Val Cys Asp Arg Gly His Glu
465                 470                 475                 480

Leu Arg Gly Ala Ile Thr Glu Glu His Arg Glu Arg Arg Thr
                485                 490                 495

Trp Trp Leu Leu Tyr Ile Met Asp Arg His Leu Ala Leu Cys Tyr Asn
            500                 505                 510

Arg Pro Leu Ala Leu Leu Asp Ala Glu Ser Glu Asp Leu Leu Leu Pro
        515                 520                 525

Leu Asp Glu Gly Ser Trp Gln Ser Gly Asn Ile His Ser Asn Ser Pro
    530                 535                 540

Lys Pro Asp Gly Pro Gln Cys Pro Leu Ser Gly Glu Lys Asn Lys Arg
545                 550                 555                 560

Arg Val Phe Pro Asn Phe Ile Cys His Asp His Ser Ile Phe Gly Phe
                565                 570                 575

Phe Leu Pro Leu Met Thr Ile Thr Gly Glu Leu Ile Asp Leu Asn Gln
        580                 585                 590

Ala Arg Asn His Pro Met Leu Gly Ala Arg Leu Asn Gly Lys Asp Ala
    595                 600                 605

Trp Asp Ala His Val Gly Glu Val Leu Arg Gln Leu Glu Leu Tyr Lys
610                 615                 620

Ala Ser Leu Thr Thr Phe Ala Ala Thr Ala Ser Asp Pro Asp Ala Pro
625                 630                 635                 640

Leu Ser Ser Ala Phe Pro Lys Pro Asp Gln Gln Pro Val Glu Pro
                645                 650                 655

Ser Leu Ala Gln Ala Tyr Ser Trp His Thr Gln Thr Val Ile Ser Tyr
        660                 665                 670

Ala Ser Tyr Leu Val His Val Leu His Ile Leu Leu Val Gly Lys Trp
    675                 680                 685

Asp Pro Val Ser Leu Ile Glu Asp Lys Asp Phe Trp Thr Ser Ser Pro
```

```
            690             695             700
Ala Phe Ala Ser Thr Ile Ser His Ala Leu Asp Ala Asp Ser Val
705             710             715             720

Asp His Ile Leu Arg Tyr Asp Pro Asp Ile Ser Phe Met Pro Tyr Phe
                725                 730                 735

Phe Gly Ile Gln Leu Leu Gln Gly Ser Phe Leu Leu Leu Ile Val
            740                 745                 750

Glu Arg Leu Gln Lys Glu Ala Gly Glu Gly Ile Leu Asn Ala Cys Glu
        755                 760                 765

Val Met Ile Arg Ala Thr Glu Ser Cys Val Val Thr Leu Asn Thr Glu
    770                 775                 780

Tyr Gln Arg Asn Phe Arg Gln Val Met Arg Ser Ala Val Ala Gln Ala
785                 790                 795                 800

Arg Gly Arg Pro Val Asn His Ser Glu Ile Arg His Arg Lys Ala
                805                 810                 815

Val Leu Ala Leu Tyr Arg Trp Thr Arg Lys Gly Thr Gly Leu Ala Leu
            820                 825                 830
```

<210> SEQ ID NO 7
<211> LENGTH: 6
<212> TYPE: PRT
<213> ORGANISM: Aspergillus sp.

<400> SEQUENCE: 7

Asn Gln Leu Arg Thr Lys
1               5

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcggggagca taatatatac aggtccagtt                                    30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgaatctcgt cttgggaagg attcaagatg                                    30

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtaaaacggc cag                                                      13

<210> SEQ ID NO 11
<211> LENGTH: 17
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 11
caggaaacag ctatgac                                                      17

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggactagtgc aggatgatcg catcgacaat tatataag                               38

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaagtctgga aggaatcagg gaaaagcaag                                        30

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aatctctcct agttctctgt tgcgctgc                                          28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tactctggta cccctccgtt gcaacaat                                          28

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atggtctcct tctcatccct tctcct                                            26

<210> SEQ ID NO 17
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 17
cggtaataga agcagatcca ctgctc                                              26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgatcttttt gtcgcggccg gcaaat                                              26

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tggcgtagct cgcagagtcc aggctaat                                            28

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgactcttg tcatgctcgc cgcgttcgat gcgac                                    35

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agagccaacc cggttccctt ccttgtccac                                          30

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggagtcgag cttgcctcga aagc                                                24

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 23
caggaagaag ccgaagatag ag                                              22

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agagccattt ggaactgggc cagaccctgc                                      30

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggctaaggac cggttctttc gc                                              22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gccgatggcc tgcggatgcg                                                 20

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atcgagcctt tcccagatct cgctgccttc gcag                                 34

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgcttgtcga cgcagccgct ctacaatcag caagagaag                            39

<210> SEQ ID NO 29
<211> LENGTH: 12
<212> TYPE: PRT
<213> ORGANISM: Aspergillus sp.

<400> SEQUENCE: 29

Glu Glu His Arg Glu Glu Arg Arg Arg Thr Trp Trp
1               5                   10
```

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctagtctaga gccctgttgc agaaatacgt cacttgggat g                          41

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tccgctcgag ctagtatgca cccttccgct tcttgtactt                            40

<210> SEQ ID NO 32
<211> LENGTH: 838
<212> TYPE: PRT
<213> ORGANISM: Aspergillus fumigatus

<400> SEQUENCE: 32

```
Met Asp Pro Ala Gln Pro Gly Asp Ala Pro Pro Thr Ser Thr Asn Thr
1               5                   10                  15

Ala Gly Thr Leu Glu Asp Ser Ser Ser Thr Ala Lys Arg Arg Trp Arg
            20                  25                  30

Arg Asn Arg Ile Ala Cys Asp Ser Cys His Ser Arg Arg Val Arg Cys
        35                  40                  45

Asp Arg Ala Phe Pro Cys Ser Arg Cys Leu Arg Ser Glu Ile Arg Cys
    50                  55                  60

Glu Phe Thr Arg Glu Arg Arg Lys Arg Gly Arg Ile Ala Arg Ser Lys
65                  70                  75                  80

Gln Thr Ala Thr Val Pro Asn Gly Gly Ser Met Glu Lys Leu Pro Lys
                85                  90                  95

Ala Pro Asn Val Gln Pro Val Pro Ala Ala Val Pro Ala Asp Ala
            100                 105                 110

Ala Pro Thr Pro Leu Pro Asn His Ala Ser Pro Thr Thr Ser Phe Gln
        115                 120                 125

His Arg Ser Pro Ala Thr Asn Glu Met Thr Val Ser Ala His Ser Ile
    130                 135                 140

Asp Asp Arg Arg Ser Gln Ala Asp Pro Ser Leu Pro Ala Arg Arg Pro
145                 150                 155                 160

Gly Pro Thr Gly Asn Val Thr Glu Glu Trp Leu Ser Ala His Val
                165                 170                 175

Ser Pro Asp Ser Tyr Glu Val Leu Gly Gly Gly Ala Trp Gly Asp Gly
            180                 185                 190

Pro Leu Pro Arg Val Leu Asp Ile Trp Asn Gly Ala Asp Leu Ala Gly
        195                 200                 205

Tyr Ser Ala Pro Thr Val Gln Ser Ser Lys Pro Ala Gly Ala Ala Arg
    210                 215                 220

Ala Pro Ser Ile Ser Ser Thr Thr Leu Lys Tyr Pro Val Leu Gln Pro
225                 230                 235                 240
```

```
Leu Met Pro Phe Leu Glu Ala Asn Leu Pro Arg Arg Leu Val Phe Asp
                245                 250                 255

Leu Leu Glu Leu Tyr Phe Thr Ser Ala Phe Ser Thr His Met His Pro
            260                 265                 270

Val Cys His His Ile His Cys Tyr Val Leu Arg Lys Ala Ser Phe Leu
        275                 280                 285

Ser Arg Glu Asn Pro Arg Pro Ser Ser Pro Ala Leu Leu Ala Ser Met
    290                 295                 300

Leu Trp Val Ala Ala Leu Asp Asp Arg Ala Phe Ala Leu Ser Ile Ser
305                 310                 315                 320

Pro Pro Gln Arg Lys Lys Ile Cys Gln Phe Leu Cys Ala Leu Thr Ile
                325                 330                 335

Arg Leu Leu Arg Pro Leu Ile His Val Ser Phe Lys Glu Gln Ala Gly
            340                 345                 350

Ser Asn Ala Ser Asp Pro Thr Phe Thr Gly Val Ala Pro Glu Cys Pro
        355                 360                 365

Pro Thr Thr Val His His Pro Phe Glu Ser Ser Gly Asp Asp Arg Gly
    370                 375                 380

Leu Val Gly Pro Ala Gly Ser Leu Asp Asp Val Ile Thr Tyr Ile His
385                 390                 395                 400

Val Ala Ser Ile Ile Ser Ser Glu Gln Lys Ala Ala Ser Met Arg
                405                 410                 415

Trp Trp His Ala Ala Phe Thr Leu Ala Arg Glu Leu Lys Leu Asn Gln
            420                 425                 430

Glu Ile Glu Val Ile Pro Asn Ala Asp Gly Gln Thr Glu Gly Ser Ser
        435                 440                 445

Pro Ala Phe Asp Tyr Ser Leu Pro Gly Trp Ser Gly Val Asp Thr Gly
    450                 455                 460

Ala Phe Phe Asp Tyr Ser Asn Pro Thr Arg Pro Ser Leu Asn Cys Val
465                 470                 475                 480

Cys Asp His Ser His Asp Pro His Ala Thr Ile Thr Glu Glu His Arg
                485                 490                 495

Glu Glu Arg Arg Arg Thr Trp Trp Leu Leu Tyr Ile Met Asp Arg His
            500                 505                 510

Leu Ala Leu Cys Tyr Asn Arg Pro Leu Ala Leu Leu Asp Ala Glu Ser
        515                 520                 525

Glu Asp Leu Leu Leu Pro Leu Asp Glu Gly Ser Trp Gln Ala Gly Asn
    530                 535                 540

Val His Ser Asn Ser Pro Lys Pro Asp Gly Pro His Cys Pro Ile Ser
545                 550                 555                 560

Gly Glu Lys Asn Lys Arg Arg Val Phe Pro Asp Phe Ile Cys His Asp
                565                 570                 575

His Ser Ile Phe Gly Phe Phe Leu Pro Leu Met Thr Ile Thr Gly Glu
            580                 585                 590

Leu Ile Asp Leu Asn Gln Ala Arg Asn His Pro Met Leu Gly Ser Arg
        595                 600                 605

Leu His Gly Lys Asp Gly Trp Asp Ala His Leu Ser Glu Val Leu Arg
    610                 615                 620

Gln Leu Glu Ile Tyr Lys Ala Ser Leu Thr Thr Phe Ala Ala Thr Ala
625                 630                 635                 640

Ala Val Pro Glu Ala Pro Leu Ala Thr Thr Tyr Arg Pro Pro Gly Pro
                645                 650                 655

Asp Pro Pro Val Glu Pro Ser Leu Ser Gln Ala Phe Ser Trp His Thr
            660                 665                 670
```

```
Gln Thr Val Ile Ala Tyr Ala Ser Tyr Leu Val His Val Leu His Ile
            675                 680                 685
Leu Leu Val Gly Lys Trp Asp Pro Val Ser Leu Ile Glu Asp Lys Asp
        690                 695                 700
Phe Trp Thr Ser Ser Pro Ala Phe Ala Thr Thr Ile Ser His Ala Leu
705                 710                 715                 720
Asp Ala Ala Asp Ser Val His Gln Ile Leu Arg Tyr Asp Pro Asp Ile
                725                 730                 735
Ser Phe Met Pro Tyr Phe Phe Gly Ile Gln Leu Leu Gln Gly Ser Phe
            740                 745                 750
Leu Leu Leu Leu Ile Val Glu Arg Leu Gln Lys Glu Ala Gly Glu Gly
        755                 760                 765
Ile Leu Asn Ala Cys Glu Val Met Ile Arg Ala Thr Glu Ser Cys Val
    770                 775                 780
Val Thr Leu Asn Thr Glu Tyr Gln Arg Asn Phe Arg Gln Val Met Arg
785                 790                 795                 800
Ser Ala Val Ala Gln Ala Arg Gly Arg Pro Val Asn His Ser Glu Ile
                805                 810                 815
Arg His Arg Arg Lys Ala Val Leu Ala Leu Tyr Arg Trp Thr Arg Lys
                820                 825                 830
Gly Thr Gly Leu Ala Leu
        835

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
1               5
```